(12) United States Patent
Vogelstein et al.

(10) Patent No.: US 9,637,779 B2
(45) Date of Patent: May 2, 2017

(54) ANTISENSE TRANSCRIPTOMES OF CELLS

(75) Inventors: Bert Vogelstein, Baltimore, MD (US);
Kenneth W. Kinzler, Baltimore, MD (US); Yiping He, Baltimore, MD (US);
Victor Velculescu, Dayton, MD (US);
Nickolas Papadopoulos, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 1096 days.

(21) Appl. No.: 13/131,413

(22) PCT Filed: Dec. 2, 2009

(86) PCT No.: PCT/US2009/066313
§ 371 (c)(1),
(2), (4) Date: Aug. 16, 2011

(87) PCT Pub. No.: WO2010/065576
PCT Pub. Date: Jun. 10, 2010

(65) Prior Publication Data
US 2012/0009573 A1  Jan. 12, 2012

Related U.S. Application Data

(60) Provisional application No. 61/119,770, filed on Dec. 4, 2008.

(51) Int. Cl.
*C12Q 1/68* (2006.01)
*G06F 19/22* (2011.01)

(52) U.S. Cl.
CPC ............ *C12Q 1/6844* (2013.01); *G06F 19/22* (2013.01)

(58) Field of Classification Search
None
See application file for complete search history.

(56) References Cited

U.S. PATENT DOCUMENTS

2007/0020633 A1 * 1/2007 Millar et al. .................. 435/6

OTHER PUBLICATIONS

Meissner et al. (2005) Nucl. Acids res. vol. 33 No. 18 pp. 5868-5877 doi:10.1093/nar/gki901.*
Taylor et al. (Sep. 15, 2007) Cancer Res. vol. 67: 8511-8518 doi:10.1158/0008-5472.CAN-07-1016.*
Invitrogen RiboMinus Tm Eukaryote kit for RNA seq manual 2008.*
Alexander Meissner. et al., Nucleic Acids Research 33(18): 5868-5877, 2005, "Reduced representation sequencing for comparative high-resolution DNA methlyation analysis".
Yiping He. et al., Science 322: 1855-1857, Dec. 4, 2008, "The Antisense Transcriptomes of Human Cells".
M. Schaefer et al. Nucleic Acids Research 37 (2). e12, Dec. 5, 2008, "RNA cytosine methylation analysis by bisulfite Sequencing".
International Search Report for PCT/US2009/066313 dated Aug. 25, 2010.

* cited by examiner

*Primary Examiner* — Aaron Priest
(74) *Attorney, Agent, or Firm* — Banner & Witcoff, LTD.

(57) ABSTRACT

Transcription in mammalian cells can be assessed at a genome-wide level, but it has been difficult to reliably determine whether individual transcripts are derived from the Plus- or Minus-strands of chromosomes. This distinction can be critical for understanding the relationship between known transcripts (sense) and the complementary antisense transcripts that may regulate them. Here we describe a technique that can be used to (i) identify the DNA strand of origin for any particular RNA transcript and (ii) quantify the number of sense and antisense transcripts from expressed genes at a global level. We examined five different human cell types and in each case found evidence for antisense transcripts in 2900 to 6400 human genes. The distribution of antisense transcripts was distinct from that of sense transcripts, was non-random across the genome, and differed among cell types. Antisense transcripts thus appear to be a pervasive feature of human cells, suggesting that they are a fundamental component of gene regulation.

34 Claims, 28 Drawing Sheets

US 9,637,779 B2

ANTISENSE TRANSCRIPTOMES OF CELLS

This invention was made using funds from the United States Government, particularly, grants from the National Institutes of Health, CA 43460, CA 57345, CA 62924, and CA 121113. The U.S. government therefore retains certain rights in the invention. The contents of provisional application Ser. No. 61/119,770, filed Dec. 4, 2008, are expressly incorporated herein.

TECHNICAL FIELD OF THE INVENTION

This invention is related to the area of expressed sequences. In particular, it relates to expression from sense and antisense strands of genes.

BACKGROUND OF THE INVENTION

The DNA in each normal human cell is virtually identical. The key to cellular differentiation therefore lies in understanding the gene products—transcripts and proteins—that are derived from the genome. For more than a decade, it has been possible to measure the levels of transcripts in a cell at the whole genome level (1). The word "transcriptome" was coined to denote this genome-wide assessment (2). However, it has been difficult to determine which of the two strands of the chromosome (Plus or Minus) serves as template for transcripts in a global fashion. Sense transcripts of protein-encoding genes produce functional proteins while antisense transcripts are often thought to have a regulatory role (3-7).

Several unequivocal examples of antisense transcripts, such as those corresponding to imprinted genes, have been described (reviewed in (3-7)). However, estimates of the fraction of genes associated with antisense transcripts in mammalian cells vary from less than 2% to more than 70% of the total genes (8-18). There is a continuing need in the art to identify expression regulatory mechanisms and agents useful for regulating expression.

SUMMARY OF THE INVENTION

According to one embodiment a method is provided for making cDNA that represents the methylation status of the RNA from which it is derived. One isolates RNA and treats the isolated RNA with bisulfite to convert at least 90% of Cytosine residues to Uracil residues. The product is termed bisulfite converted RNA. The product is reverse transcribed to form cDNA which represents the methylation status of the RNA.

According to another embodiment a method is provided for preparing non-complementary products from two complementary DNA strands. RNA transcribed from two complementary DNA strands is obtained and treated with bisulfite to convert at least 90% of Cytosine residues to Uracil residues. Again the product is termed bisulfite converted RNA. First strand DNA is synthesized using the bisulfite converted RNA as a template by reverse transcription. Second strand DNA is synthesized using the first strand DNA as template. Double-stranded DNA molecules are formed from first and second strand DNA.

According to one embodiment a method is provided of identifying the template strand of a transcribed sequence. RNA is isolated. The RNA is treated with bisulfite to convert at least 90% of Cytosine residues to Uracil residues, thereby forming bisulfite converted RNA. The nucleic acid base sequence of at least a portion of said bisulfite converted RNA is determined. The determined nucleotide sequence data of the bisulfite converted RNA is compared to and matches are identified with sequence data of a strand of DNA. The sequence data have been transformed in silico by changing Cytosine residues to Uracil residues. Based on identified matches, one can determine whether a determined nucleotide sequence was transcribed from the strand of DNA.

According to one embodiment, a method is provided for identifying an expressed RNA as sense or antisense. Bulk expressed RNA is isolated from a cell sample. Ribosomal RNA (e.g., 18S and 28 S rRNA) are removed from the bulk expressed RNA to form rRNA-depleted RNA. The rRNA-depleted, expressed RNA is treated with bisulfite to convert at least 90% of Cytosine residues to Uracil residues, forming converted RNA. A first strand DNA is synthesized using converted RNA as a template for reverse transcription. A second strand DNA is synthesized using first strand DNA as template. Double-stranded DNA molecules are formed from first and second strand DNA. The double stranded DNA molecules are used to determine nucleotide sequence of at least portions of the double-stranded DNA molecules. Determined nucleotide sequence of the double-stranded DNA molecules and a database of human genomic sequence that has been transformed by changing Cytosine residues to Uracil residues are compared and matches are identified between the sequences. Based on identified matches it is determined whether a determined nucleotide sequence was transcribed from a coding (sense) or a non-coding (antisense) strand of a gene.

According to another embodiment a method is provided for preparing non-complementary products from two complementary DNA strands. RNA transcribed from two complementary DNA strands is isolated. The RNA is treated with bisulfite to convert at least 90% of Cytosine residues to Uracil residues, forming converted RNA. First strand DNA is synthesized using converted RNA as a template for reverse transcription. Second strand DNA is synthesized using first strand DNA as template. Double-stranded DNA molecules are formed from first and second strand DNA.

A machine implemented process is provided in which an individual piece of gene sequence datum is compared to a database. The database comprises genomic sequence that has been transformed in silico by changing Cytosine residues to Uracil residues. The individual piece of gene sequence datum is obtained from RNA that has been treated in vitro with bisulfite to convert at least 90% of Cytosine residues to Uracil residues. A match is identified when at least 34 out of 36 contiguous residues are identical.

Also provided as an embodiment of the invention is a programmed computer. The computer comprises a memory comprising a database of genomic sequence that has been transformed in silico by changing Cytosine residues to Uracil residues. It also comprises a processor which compares input sequences to the database and scores matched bases. It further comprises an output that indicates matched bases.

These and other embodiments which will be apparent to those of skill in the art upon reading the specification provide the art with methods and tools for isolating and identifying transcribed RNA sequences.

DETAILED DESCRIPTION OF THE INVENTION

Figure 3A:
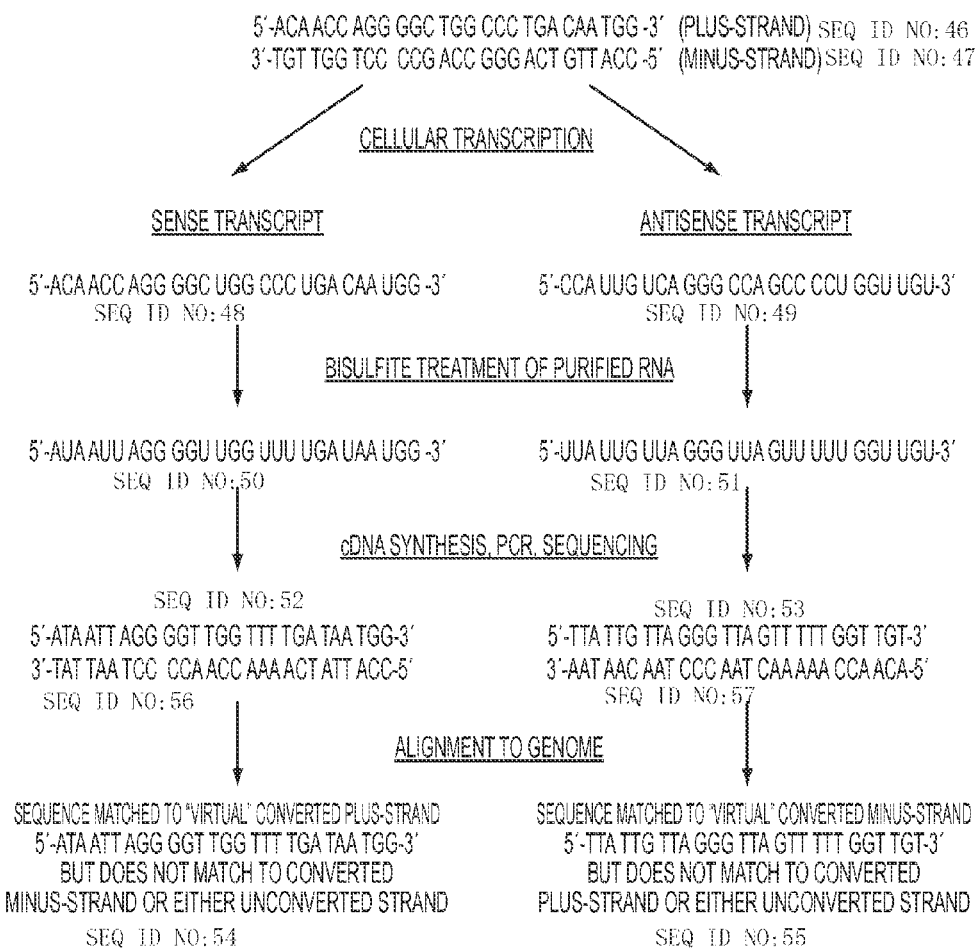
FIG. 3A-B. Principles of ASSAGE
Figure 3B:
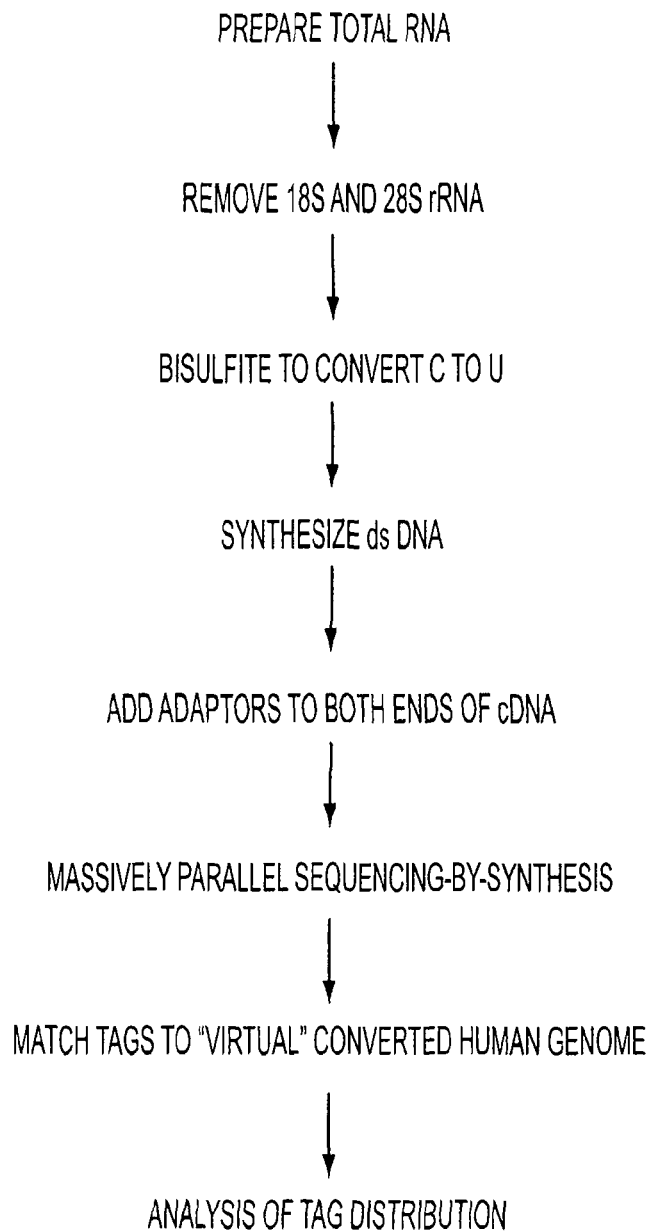
Figure 4A:
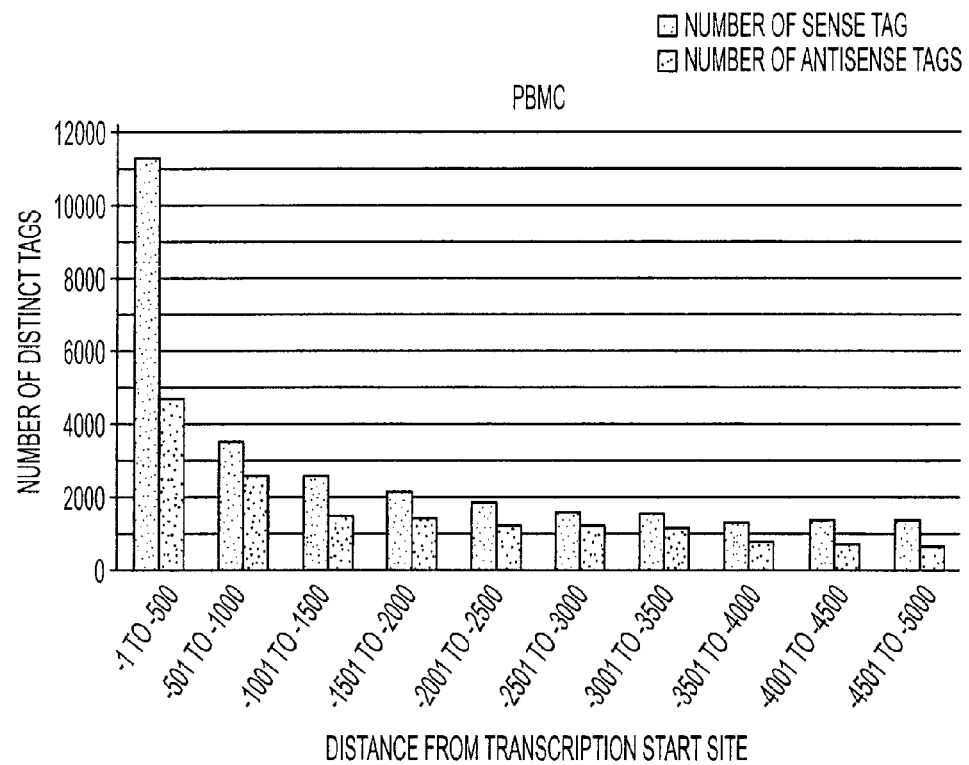
FIG. 4A-4E. Distribution of tags located in promoter and terminator regions of genes in the indicated samples.
Figure 4A:
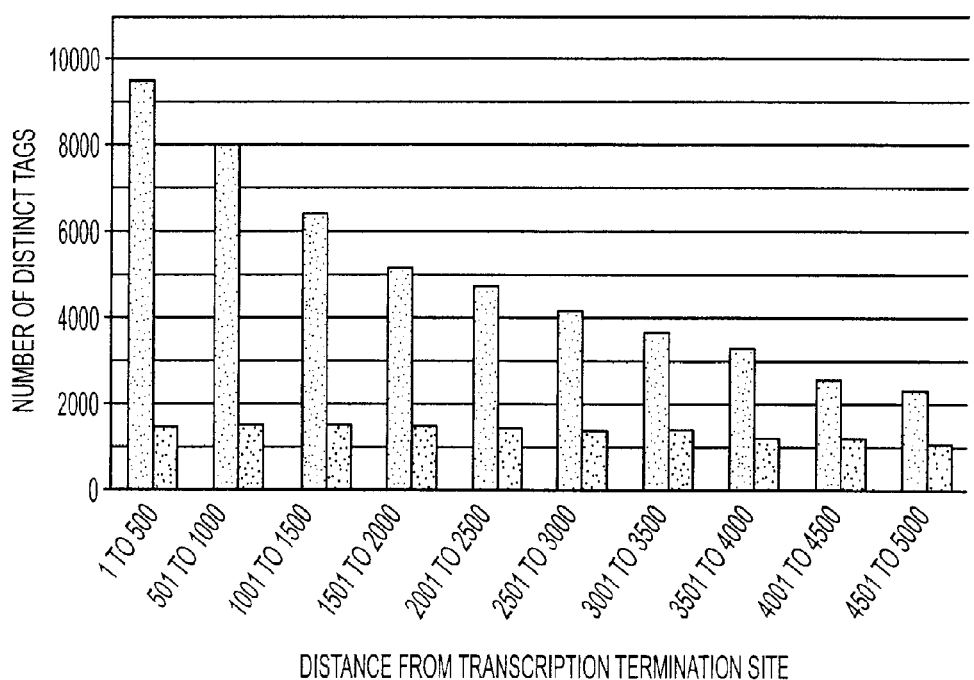
Figure 4B:
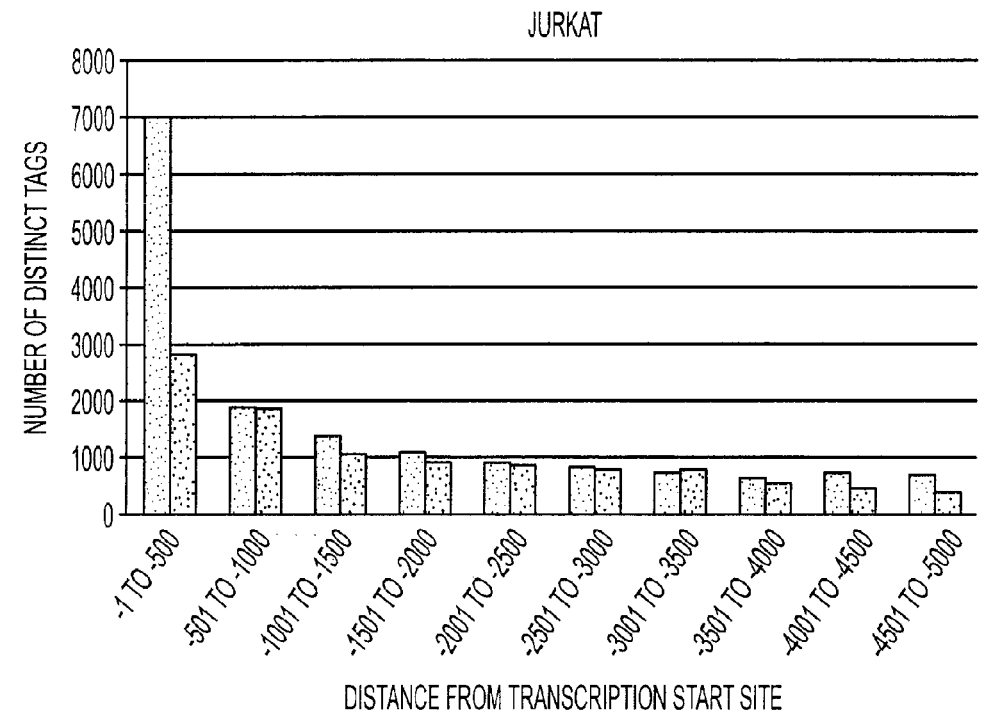
Figure 4B:
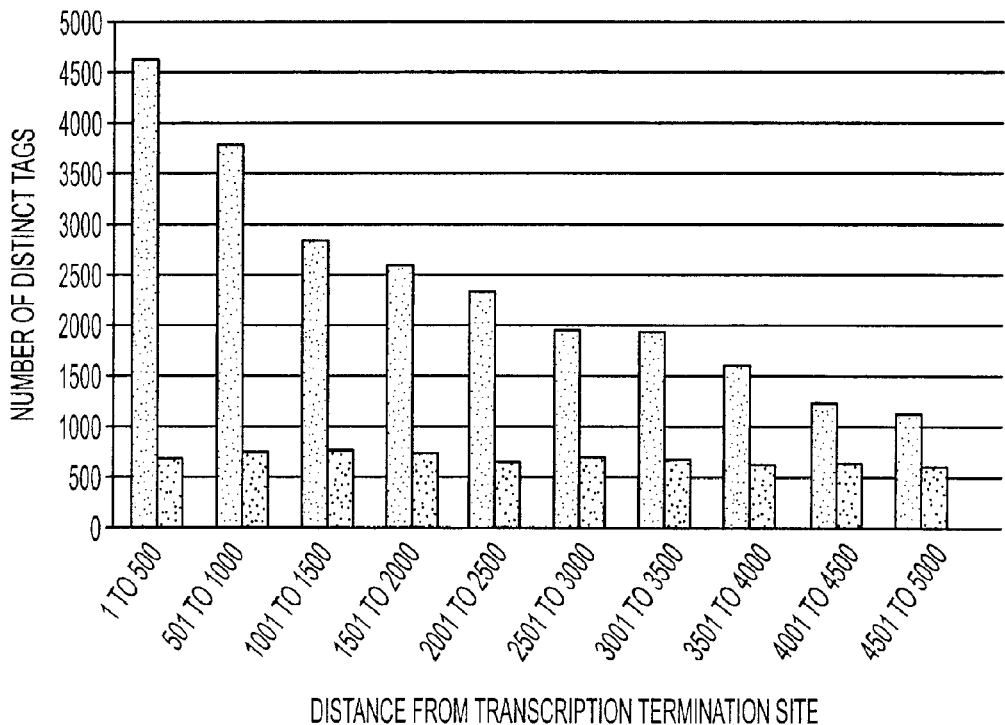
Figure 4C:
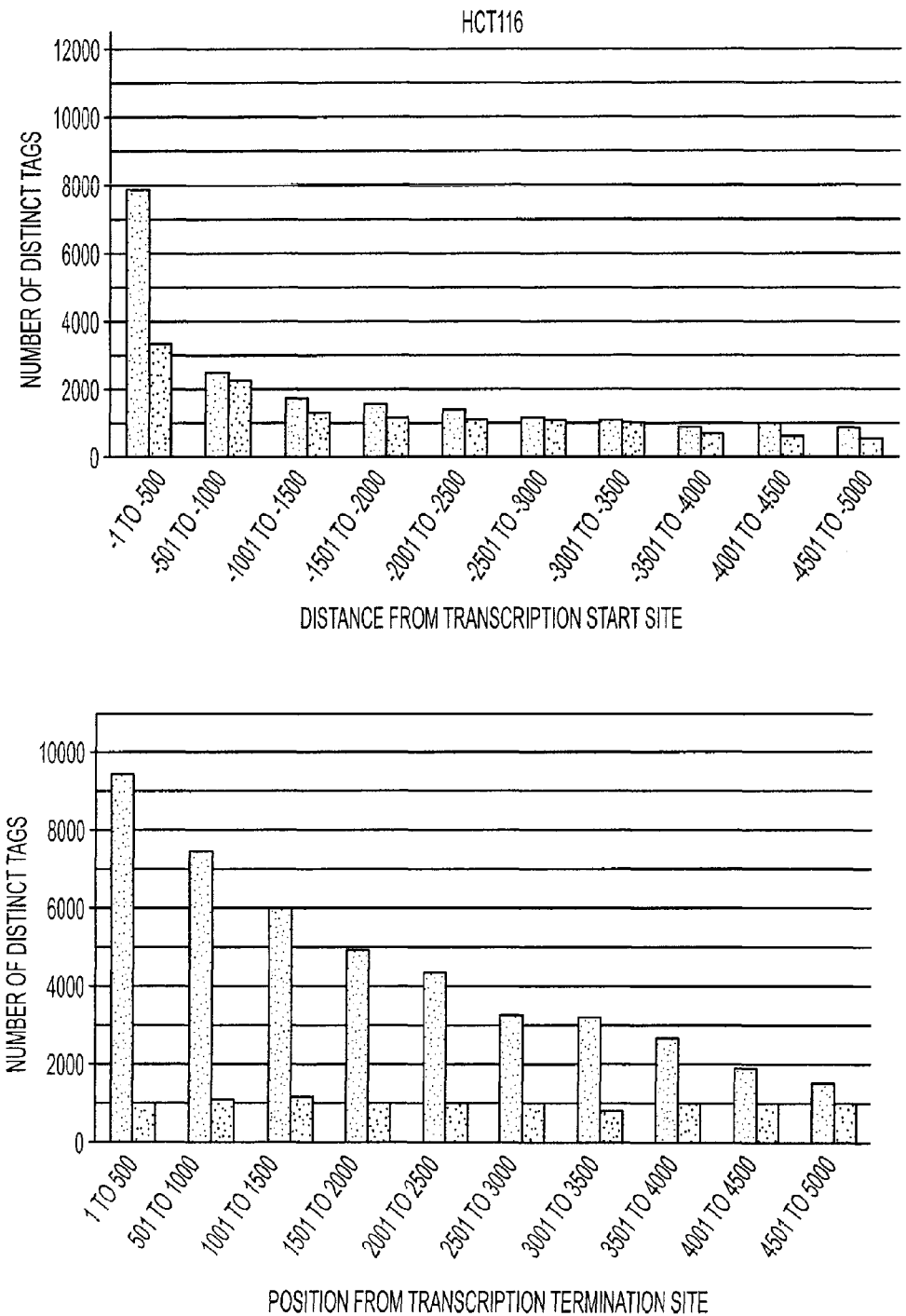
Figure 4D:
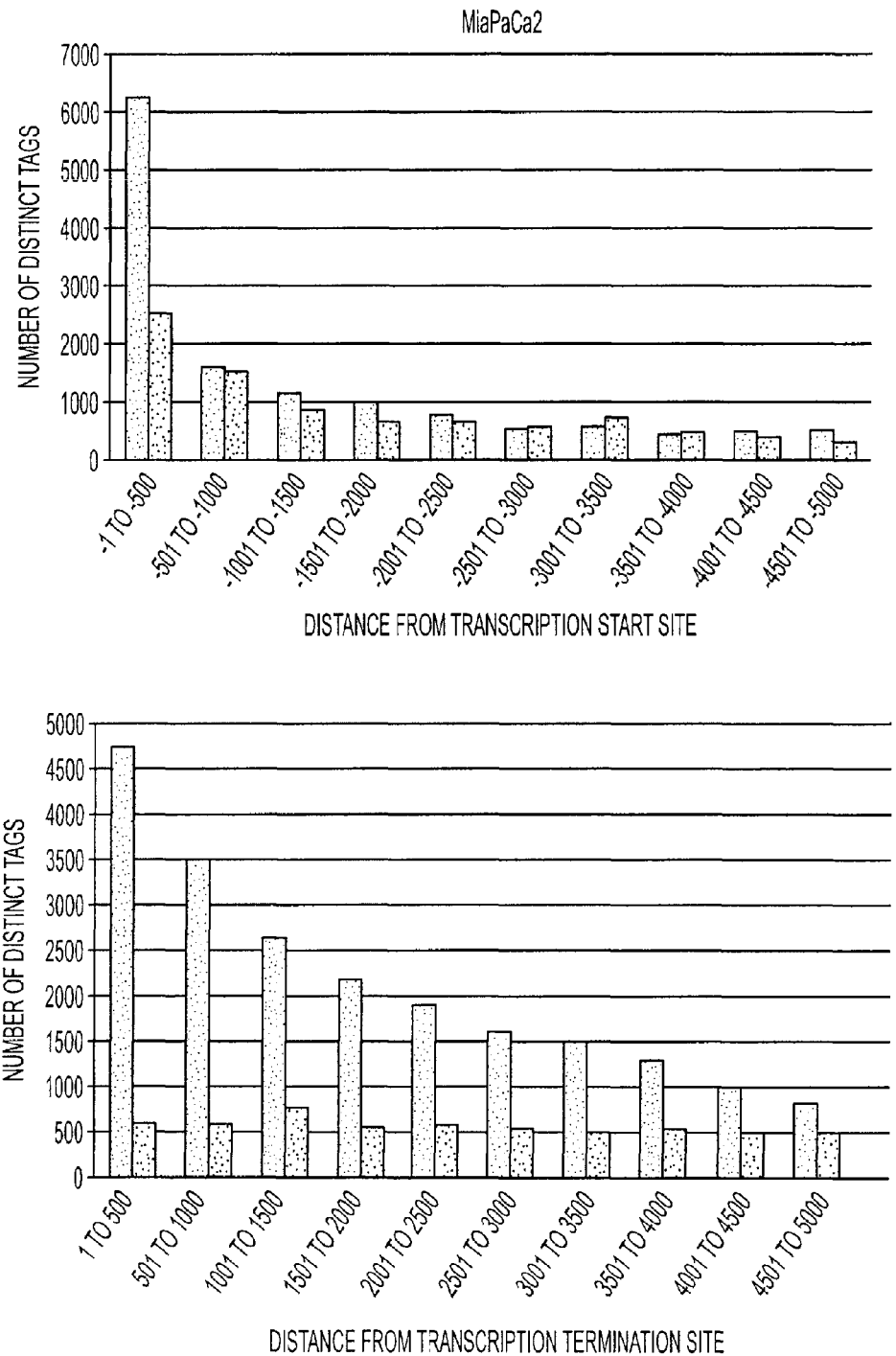
Figure 4E:
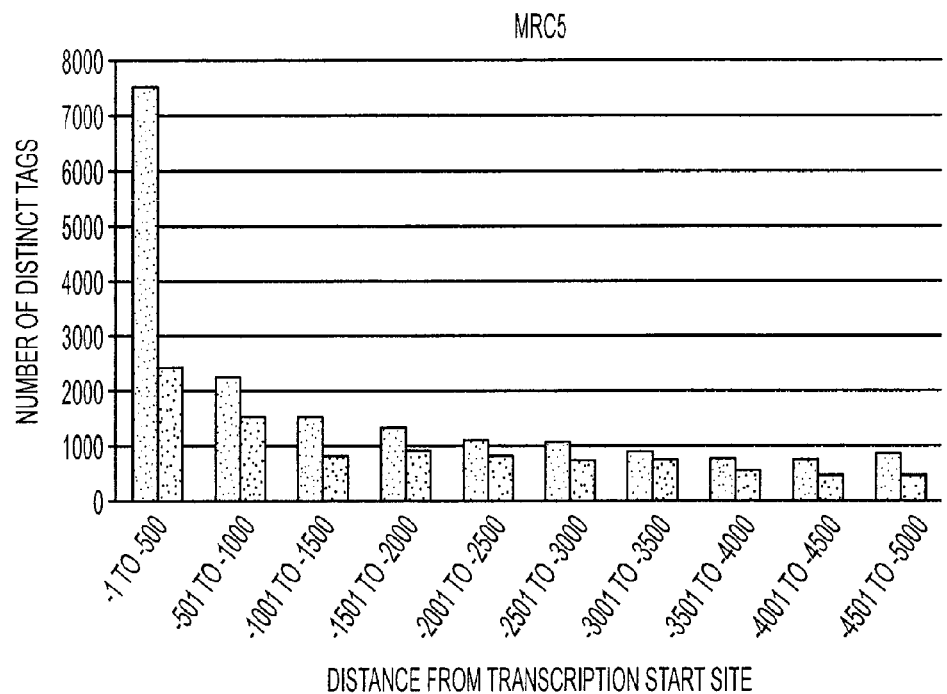
Figure 4E:
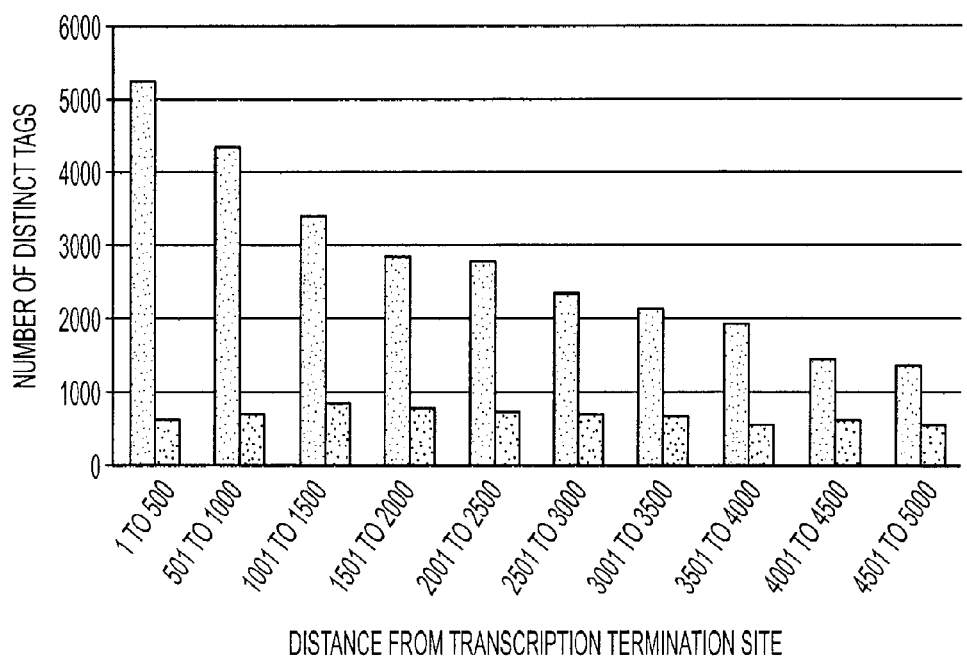

We have developed a technique called ASSAGE (Asymmetric Strand Specific Analysis of Gene Expression) that allows unambiguous assignment of the DNA strand coding for a transcript. The key to this approach is the treatment of RNA with bisulfite, which changes all (or almost all) cytidine residues to uridine residues. The sequence of a bisulfite-treated RNA molecule can only be matched to one of the two possible DNA template strands (FIG. 3). After generating cDNA from bisulfite-treated RNA with reverse transcriptase (RT), sequencing of the RT-PCR product can be used to establish whether a particular RNA was transcribed from the Plus- or Minus-strand. To identify the DNA strands of origin for the entire transcriptome, cDNA fragments derived from bisulfite-treated RNA can be ligated to adapters and the sequence of one end of each fragment can be determined, e.g., through sequencing-by-synthesis. The number and distribution of the sequenced tags provide information about the level of transcription of each gene in the analyzed cell population as well as the strand from which each transcript was derived.

Figure 1:
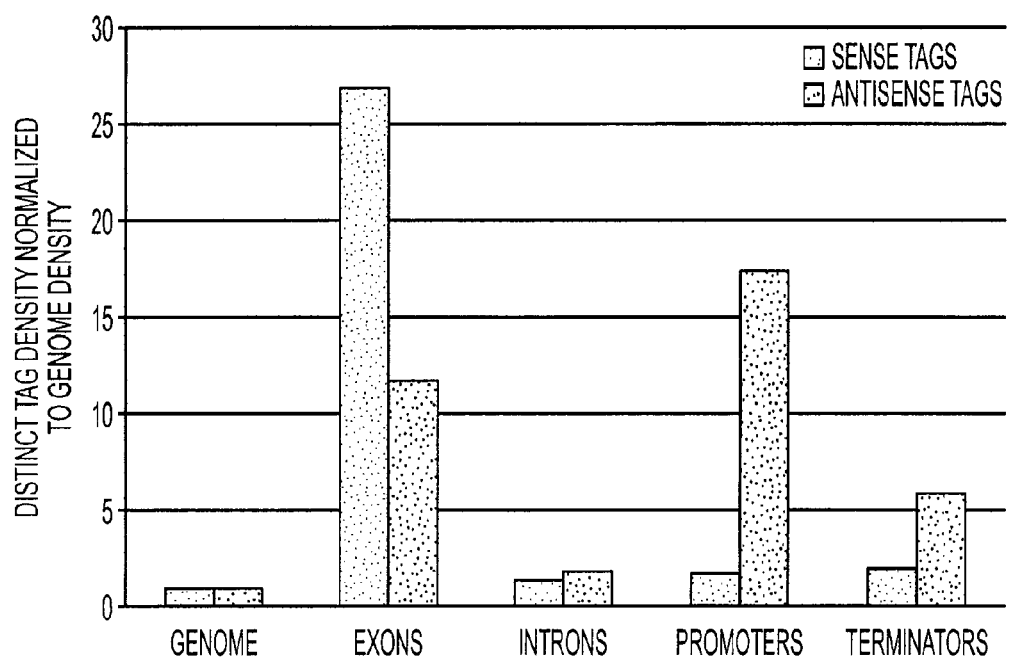
FIG. 1. ASSAGE tag densities in PBMC. The density of distinct sense and antisense tags in the indicated regions were normalized to the overall genome tag density. The promoter and terminator regions were defined as the 1 kb of sequence that was upstream or downstream, respectively, of the transcript start and end sites.

Our results raise many questions about the genesis and metabolism of antisense transcripts. It has been hypothesized that antisense transcripts are widely and promiscuously expressed, perhaps due to weak promoters distributed throughout the genome (reviewed in (25, 26)). Our data argue against this hypothesis in human cells: promiscuous expression would lead to a uniform distribution of antisense tags across the genome, while the observed distribution was non-random, localized to genes and within particular regions of genes, much like sense transcripts (FIGS. 1, 4, and 10). This distribution is consistent with a model wherein many antisense transcripts initiate and terminate near the terminators and promoters, respectively, of the sense transcripts. Some of the apparent antisense transcripts from a gene on the Plus-strand could actually be sense transcripts originating from unterminated transcription of a downstream gene on the Minus-strand (or vice versa). However, this idea is not generally supported by the poor correlation between antisense tag density within a gene and the density of sense tags from the closest downstream gene (FIG. 15). One explanation for the higher density of antisense tags in transcribed regions is that transcription of the sense transcripts from correct initiation sites would reduce nucleosome density throughout the entire transcribed region, thereby increasing DNA accessibility and hence the likelihood of non-specific transcription (26). This is unlikely given that genes with high sense tag densities did not generally have high antisense densities. There is substantial evidence that sense transcripts can be negatively regulated by antisense transcripts (3-7). Such regulation can occur either by transcriptional interference or through post-transcriptional mechanisms involving splicing or RISC-like processes. Our data support the possibility that antisense-mediated regulation affects a large number of genes.

Cells which can be used as a source of bulk RNA include any of any kingdom, including bacteria, archaebacteria, fungi, plants, parasites, viruses, lower animals, mammals, reptiles, primates, farm animals, laboratory animals, humans, and pets. Methods for isolating RNA from cells are well known and these can be used. Bulk RNA refers to unfractionated or total RNA from a cell. It can have various functions and can be from various genes. Ribosomal RNA forms the majority of bulk RNA and in some analyses obscure an analysis of other types of RNA. Ribosomal RNA can be removed from the bulk RNA using any technique known in the art. Typically these techniques are based on hybridization, but other purification methods can be used, for example size-based separation. Poly-A selection can be used, for example to isolate mRNA. Expressed RNA refers to those molecules which are transcribed from a gene for any purpose, whether forming, for example, a regulatory RNA, a tRNA, an rRNA, a transcript, or a no-known-function RNA. RNA can also be generated in cell-free systems. Such RNA may be transcribed in vitro, for example, from double-stranded DNA or RNA genomes.

Treating RNA with bisulfite is known in the art. We provide a particular protocol that we found efficient at the conversion of cytosine residues to uracil residues. However, other protocols may be used. Preferably the conversion is so complete as to convert at least 90%, at least 91%, at least 92%, at least 93%, at least 94%, at least 95%, at least 96%, at least 97%, at least 98%, or at least 99% of the cytosine residues.

Reverse transcription of RNA using a reverse transcriptase enzyme and deoxyribonucleotides is known in the art. Any particular method or particular enzyme that catalyzes this reaction can be used. After first strand of copy DNA (cDNA) is formed using the reverse transcriptase enzyme, second strand cDNA can be formed using a DNA polymerase enzyme and deoxyribonucleotides. Any such particular protocols can be used to prepare the double stranded cDNA.

The sequence of converted RNA can be determined directly by RNA sequencing or indirectly by sequencing cDNA copied from the converted RNA. The sequence of the individual fragments and strands of double stranded cDNA can be determined using any technique known in the art. One such technique is sequencing-by-synthesis. Preferably the sequencing is performed in a massively parallel fashion. The entire length of the individual fragments need not be sequenced. In one embodiment, only a set number of nucleotides from an end is determined. Such a set number of nucleotides is termed a tag which is characteristic of a transcript. Tags may be, for example, at least 14, at least 18, at least 22, at least 26, at least 30, at least 34 nucleotides in length. Other means of sequence determination may employ controlled chemical degradation, enzymatic synthesis with inhibitors or terminators, ligation, hybridization to arrayed probes, etc.

Databases of in silico-converted sequences can be made by converting Cytosine residues to Uracil residues. To represent the opposite strand, sequences can be separately in silico-converted so that Guanine residues are Adenine residues. These databases are used to compare, match, and align to the in vitro converted RNA sequences and their cDNA correspondents. The comparing and matching can be done by human or by machine. One software package which can be used is the Eland™ software of Illumina. Once a sequence representing an in vitro converted RNA has been matched to an in silico converted sequence, one can readily identify whether the sequence is a sense or an antisense molecule. Sense sequences are those that match genomic positions between the start and end sites of the same strand of a known transcript or in its promoter or terminator. Antisense sequences are those which match positions on the opposite strand of a known gene. Some RNA molecules may match to regions of the genome which are not annotated.

Splicing of antisense RNA molecules can be identified. RNA fragments that contain portions that align with genomic sequences that are more distant than the portions are in the RNA molecule are indicative of splicing. Practically, the portions must both align to portions of one gene only (not align promiscuously), must match to the same gene, and must match to the same strand of the gene. These criteria should reduce artifactual results. The criterion of distance that separates the portions may be set as desired. The distance of separation may be any distance greater than zero, but may be set as a fixed distance, e.g., at least 100, 500, 1,000, 10,000, or 100,000 nucleotides. Alternatively, the distance may be set relative to the size of the RNA molecules sequenced or relative to an average of the RNA molecule population sequenced.

Figure 16:
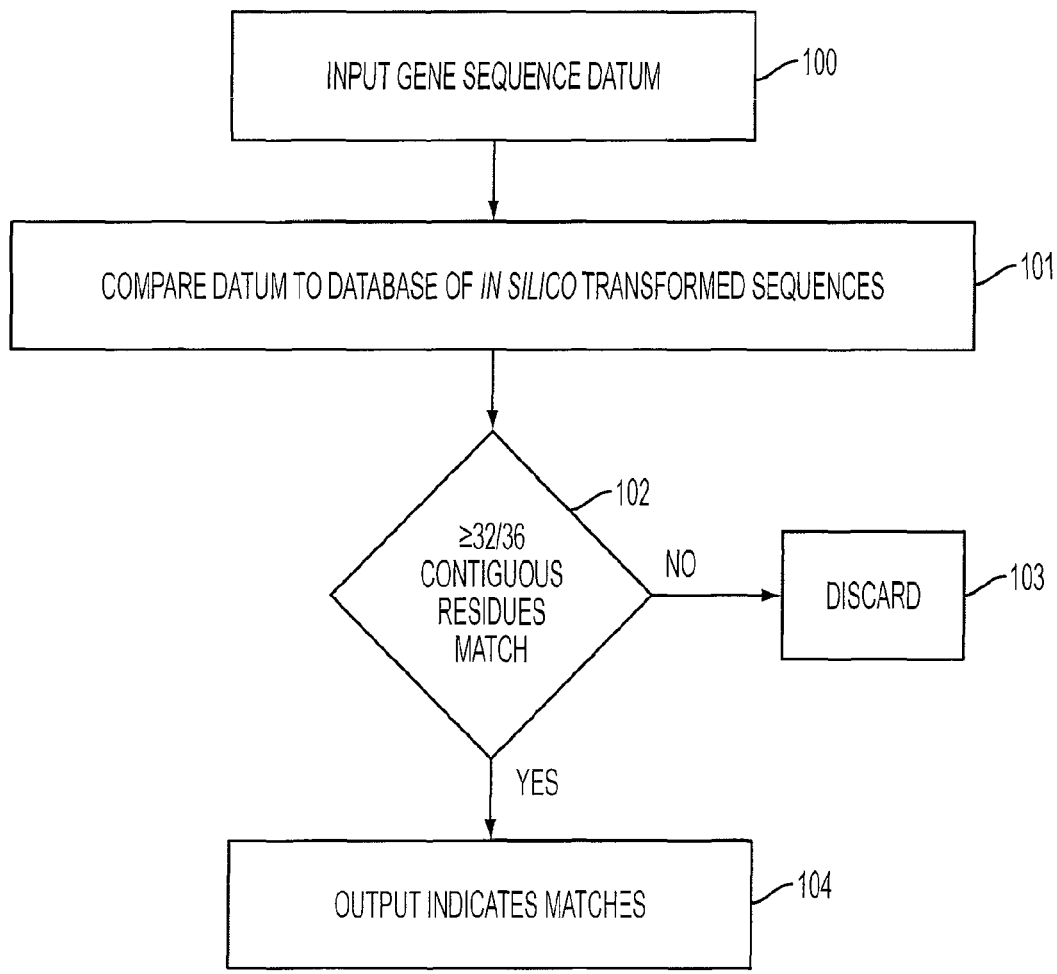
FIG. 16. Schematic of computer implemented process for matching experimentally converted sequences to in silico converted sequences.
Figure 17:
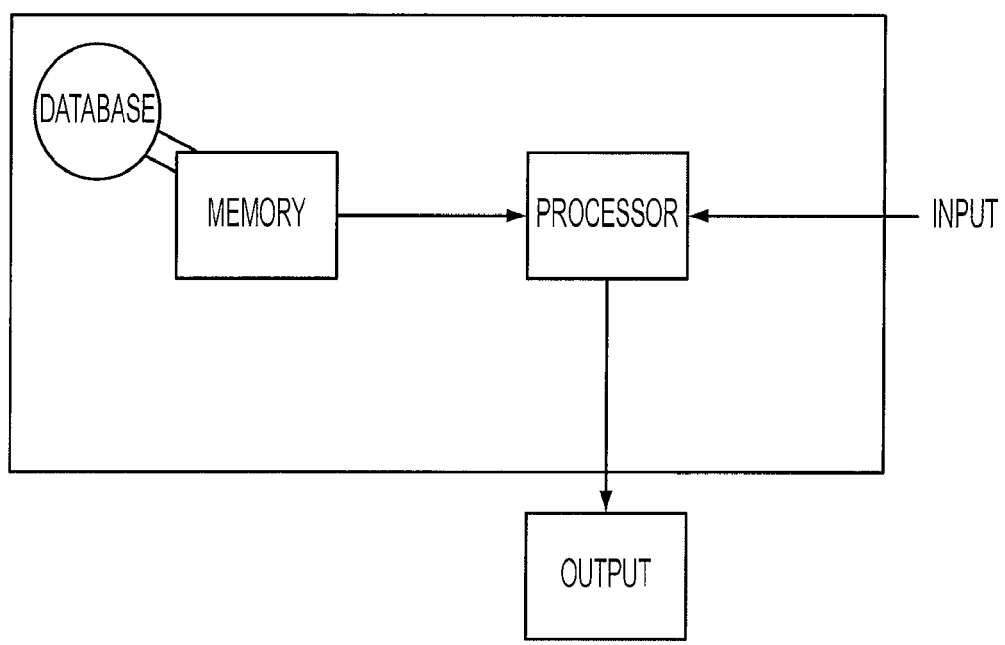
FIG. 17. Programmed computer for matching experimentally converted sequences to in silico converted sequences.

Comparison of experimentally generated converted sequences to virtually converted sequences can be performed manually or by machine as shown in FIGS. 16 and 17. A computer can be programmed to compare an individual sequence that was experimentally determined (input gene sequence data, 100) to a database of virtually converted sequences that are stored in a computer memory. (Compare to database, 101) The database may represent the strand which was bisulfate converted and/or the complement of that strand. The database may represent two converted strands and their complements. One set of virtual sequences has cytosines converted to uracils, and the other set of sequences has guanines converted to adenines. The database may be within the computer or at a remote storage device, for example, one that is accessible via the internet. See FIG. 17. Identity criteria can be set by the operator, as desired. A processor may perform the comparison using various algorithms which are known in the art for comparing nucleic acid sequences (101). While various lengths for matching and stringency of matching can be used, one useful criterion is a level of at least 32/36 contiguous matches (102). Other criteria may be desirable under certain circumstances, either increasing or decreasing the stringency of matching or increasing or decreasing the length over which a matching ratio is determined. Lengths which may be used include at least 10, 15, 20, 25, 30, 35, 40, 45, 50, 55, 60, or 65 bases.

Matching ratios which may be used include at least 80%, 85%, 88%, 89%, 90%, 95%, 97%, 98%, or 99%. Non-matching sequences are discarded (103), and matching sequences are indicated to a user. An output displays the results of the comparison (104). Typically the output is visual, such as a display or a printer for making a printed representation of sequence identity. However, other forms of output are possible, including but not limited to an audible or tactile representation of the comparison results. Results can also be stored for later assembly and/or access.

Because the conversion of cytosine bases by bisulfite may not be quantitative, the matching and aligning process may need to employ lowered stringency. Identity criterion can be set, for example, as at least 85%, at least 87%, at least 89%, at least 91%, at least 93%, etc. Lengths which may be used include at least 10, 15, 20, 25, 30, 35, 40, 45, 50, 55, 60, or 65 bases. Matching ratios which may be used include at least 80%, 85%, 88%, 89%, 90%, 95%, 97%, 98%, or 99%. As length is changed, the stringency may be changed to compensate.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Materials and Methods

Samples and RNA Preparation

DNA-free total RNA from Jurkat T cell-leukemia line and MRC5 diploid lung cell line were purchased from Ambion (Austin, Tex.). The colorectal cancer cell line HCT116 and pancreatic cancer cell line MiaPaCa2 were purchased from ATCC (Manassas, Va.) and were grown in McCoy's 5A medium with 10% fetal calf serum. Normal human peripheral blood mononuclear cells (PBMC) from a healthy volunteer were isolated from fresh peripheral blood with Histopaque-1077 (Sigma, St. Louis, Mo.). Total RNA from PBMC, HCT116 and MiaPaCa2 was isolated with the RNeasy kit (Qiagen, Valencia, Calif.) according to the manufacturer's instructions. The DNA was removed from the total RNA preparation with the DNA-free kit (Ambion).

Total RNA was enriched for the non-ribosomal fraction by treating 20-24 ug of DNA-free total RNA with the RiboMinus transcriptome isolation Kit (Invitrogen, Carlsbad, Calif.). To remove as much ribosomal RNA (rRNA) as possible, two rounds of rRNA reduction were performed. Subsequently, the RNA was ethanol-precipitated, washed in 70% ethanol, re-suspended in RNase-free water, and finally eluted in RNase-free water from a RNeasy column. To confirm that each RNA sample was DNA-free and to evaluate the effectiveness of rRNA removal, RT-PCR was performed with reagents from SuperScript Vilo cDNA synthesis Kit (Invitrogen) according to the manufacturer's recommendations. The efficiency of RNA removal was evaluated by qPCR using primers that resulted in the amplification of either 18S ribosomal RNA or specific mRNA species. We found that ~90% of 18S and 28S rRNA was successfully removed by the procedure described above.

Bisulfite Conversion of RNA

RNA enriched for the rRNA-depleted fraction was treated with bisulfite according to a modified protocol based on the EpiTect Bisulfite Kit (Qiagen). Twenty ul of rRNA-depleted RNA (corresponding to 12-15 ug total RNA) was mixed with 85 ul of Bisulfite Mix and 35 ul of Protect Buffer. The conversion of C to U was performed by heating the solution under the following conditions: 99° C., 5 min; 60° C., 25 min; 99° C., 5 min; 60° C., 85 min; 99° C., 5 min; 60° C., 155 min. Following completion of the reaction, the converted RNA was desalted by following steps: (i) the mix was diluted with RNase-free water to a total volume of 15 ml and concentrated to 0.67 ml using Centriprep Ultracel YM-3 15 ml filter (Millipore, Bedford, Mass.) by three sequential centrifugations at 3000 g, room temperature for 95 min, 30 min and 10 min; (ii) the RNA was ethanol-precipitated, washed in 70% ethanol and re-suspended in 15 ul RNase-free water; (iii) the recovered RNA was mixed with 300 ul of 0.5 M Tris-HCl (pH 9.0) and incubated at 37° C. for 60 min for de-sulfonation (W. Gu, R. L. Hurto, A. K. Hopper, E. J. Grayhack, E. M. Phizicky, Mol Cell Biol 25, 8191 (2005).); and finally, (iv) the treated RNA was ethanol-precipitated, washed in 70% ethanol, and resuspended in 30 ul RNase-free water.

Library Preparation for Sequencing by Synthesis

Double stranded cDNA was synthesized from the converted RNA using regular random hexamer (for RNA-seq library construction) or random octamers comprised of only three bases (A, C, T) (for ASSAGE library construction) and Superscript III reverse transcriptase (Invitrogen), following the manufacturer's recommendations for preparation of double-stranded cDNA. Specifically, for ASSAGE library construction: (i) we used a random octamer mix of (H)7A:(H)7C:(H)7T, (where H=A, C, or T) at 2:1:1 molar ratio as primer for first-strand cDNA synthesis: 30 ul of converted RNA was mixed with 4.5 ul of water and 1.5 ul containing 400 ng of random octamer mixture; the mixture was incubated at 70° C. for 10 min and cooled in ice for 3 min; (ii) the denatured RNA/oligo was mixed with 12 ul of 5× first strand buffer, 6 ul of 0.1M DTT, 3 ul of 10 mM dNTP; 0.3 ul of 100 mM dATP and 1.5 ul of RNaseOut; (iii) the mixture was incubated at 45° C. for 2 min before 3 ul of Superscript III retro-transcriptase was added; (iv) the mixture was incubated at 45° C. for 1 hour before being cooled at ice for 3 min; (v) the first-stranded cDNA was mixed with 61.5 ul of water, 15 ul of GEX 2nd strand buffer (Illumina), 4.5 ul of 10 mM dNTP, 0.45 ul of 100 mM dTTP, 6 ul of DNA polymerase I (Illumina), 1.5 ul of RNaseH, and 1.5 ul of E. coli DNA ligase (Invitrogen); (vi) total of 150 ul mixture was incubated at 16° C. for 2 hours; (vii) 3 ul of T4 DNA polymerase was added to the mix and the reaction was incubated at 16° C. for 5 min to complete the double-stranded cDNA synthesis. Double-stranded cDNA was cleaned up by QIAquick PCR purification column (Qiagen) and eluted in 70 ul of elution buffer (EB).

The double-stranded cDNA was used to construct libraries for sequencing following Illumina's standard genomic DNA sample preparation instructions. Briefly, this procedure consists of six steps: (i) double-stranded cDNA in 70 ul of EB was mixed with 700 ul of nebulization buffer and fragmented by nebulization; (ii) the ends of the fragmented double-stranded cDNA were blunt-ended with T4 DNA polymerase, Klenow polymerase, and T4 polynucleotide kinase; (iii) a dA was added to the 3' and of each strand by Klenow (exo −) polymerase; (iv) adapters designed for library construction from genomic DNA available from Illumina were ligated to the cDNA fragments; (v) ligation product was gel-purified to select for ~120-200 bp fragments; and (vi) PCR amplification to enrich ligated fragments. For sequencing, the library was denatured with 0.1 M NaOH to generate single-stranded DNA molecules, captured on Illumina flow cells, amplified in situ and subsequently the ends of the fragments were sequenced for 36 cycles on an Illumina Genome Analyzer. A similar library (RNA-seq library) made from the rRNA-depleted RNA of PBMC in the absence of bisulfite treatment was used as control to determine bisulfite-conversion efficiency and the potential effect of bisulfite on the sense transcriptome (see main text).

For paired-end (PE) sequencing, PE-ASSAGE libraries were constructed using Illumina PE-genomic DNA library kit, following the protocol for ASSAGE library described above with modification. Specifically, PE adaptors were used at the ligation step; and the pre-amplified library after the ligation was resolved by agarose gel to select fragments of ~300 bp in length (including adapters), which was then gel-purified for final library amplification. Sequencing of PE-ASSAGE library was performed following Illumina's Solexa protocol.

Efficiency of Bisulfite Conversion of C to U

First, the A, C, G, and T content of the transcriptome was determined through sequencing 3.27 million quality-controlled tags (118 million bases) generated from PBMC RNA in the absence of bisulfite treatment. These tags had high chastity scores according to Illumina criteria and matched the human genome. The C/G and A/T contents of these tags were 48% and 52%, respectively. Next, random subsets of 50,000 of these 36-base sequences were used to determine the fraction of 36-base tags that should contain Gs but no Cs after various conversion efficiencies using Monte Carlo simulations. The fraction of tags that contain Gs but do not contain Cs provides a measure of conversion efficiency. From these simulations, a 95% conversion rate (±1%) was determined to be most consistent with the number of observed for 36-base tags that contained Gs but not Cs in the actual experimental libraries prepared from bisulfite-treated RNA.

Data Analysis

The sequences generated were aligned independently to the human genome (release hg18) and transcript databases (RefSeq release 35) using the Illumina alignment software Eland. The reference sequence for the alignment was modified in silico to simulate a genome in which all Cs had been converted to Ts by bisulfite treatment. Two versions of the human genome were generated: one in which all of the Cs were changed to Ts (representing the converted Plus-strand of DNA of each chromosome according to hg18) and the other in which all of the Gs were changed to As (representing the complement of the converted Minus-strand of each chromosome). We similarly created two converted versions of the RefSeq sequences. All experimentally-identified sequences were matched to both versions of the modified genome, both versions of the RefSeq sequences, and in some cases to the normal (unconverted) genome and RefSeq sequences. The alignment was performed with the Eland software using the eland extended module which matches 32 bases and then explores the alignment of the remaining 4 bases of the 36 base tags. Although the matching is based on 32 bases, the sequences with 36 perfect matches receive better scores than those that match 32 to 35 bases. The following criteria were used to filter the tags for further analysis: Each tag was required (i) to pass the Illumina chastity filter; (ii) not to match to rRNAs or t-RNAs; and (iii) to match uniquely to one of the two converted versions of the genome with no more than two mismatches (thus defining a "unique" tag).

Analysis of Tags and Transcript Mapping

Each tag was assigned to a gene from the Ensembl ensGene database (found at hypertext transfer protocol http://, domain name hgdownload.cse.ucsc., extension edu/ webpage location on domain goldenPath/hg1 8/database/ ensGene.txt.gz) by virtue of its unique genomic position. Promoter and terminator regions of the genes were defined as those sequences which mapped one kb upstream or one kb downstream from transcription 'start' and 'end' sites, respectively. The tags were classified as sense or antisense. Sense tags were defined as those that matched genomic positions between the 'start' and 'end' sites of the same strand of a known transcript annotated in the Ensembi database or in it promoter or terminator as defined above. Antisense tags were defined as those that matched positions on the opposite strand of a known gene. Distinct tags that matched to regions of the genome that were known to produce transcripts from both strands were considered ambiguous and were excluded from further analysis. Tags that could not be classified in any of the above categories were labeled as non-annotated. Tag densities in exons, intrans, and other generic regions were compared using t-tests.

To estimate the theoretical percentage of converted tags that could be uniquely matched to the reference genome, two sets of virtual 36-base tags were generated in silico. The first set included 1.6 million tags covering the sequences of each strand of the transcripts that were used as examples in FIGS. 2, 5 and 7 as well as arbitrarily selected transcripts from elsewhere in the genome. The second set included 4.8 million tags representing the two strands from random areas of each chromosome (100,000 sequences from each strand of every chromosome). In each of these sets, all C's were changed to Ts to mimic the effects of bisulfite-conversion. We performed a similar in silico experiment to determine the fraction of tags that should map to the genome in the absence of bisulfite conversion. For this determination we used virtual tags derived from the set of 4.8 million tags described above but did not change the Cs to Ts. We found that 52% of the tags expected to be derived from ASSAGE could be assigned to a unique genomic position. 71% of virtual tags generated in the absence of conversion could be uniquely assigned, with the remainder assigned to more than one genomic position. The proportion of converted tags that could not be uniquely matched was higher because of the three-base rather than four-base code, allowing a portion of closely-related gene sequences to produce identical virtual tags. Nevertheless, the process of converting a four-base to a three-base code only moderately reduced the tag information content and still allowed assignment of tags to unique genomic positions.

The procedure for matching PE-ASSAGE tags was performed similarly to that described above in the Data Analysis section. To assess potential transcript splicing, we required that the two tags (tag1 and tag2) representing each end of the cDNA fragment were unique and matched to the same gene and the same orientation (sense or antisense). The average distances separating tag1 and tag2 in sense transcripts was 169 and 182 bp in the Jurkat and MRC5 libraries, respectively, as determined by mapping to the human transcript (not genomic) database. Analysis of the distribution of PE tags with respect to the genomic distances separating tag1 and tag2 from individual cDNA fragments provided an estimate of the fraction of sense or antisense tags that resulted from splicing.

RNA Microarray Expression Analysis

Fractions of the same RNA preparations used to construct ASSAGE libraries were used for the generation of cRNA for microarray analysis on Agilent chips. Briefly, total RNA was reverse transcribed by MMLV-RT using an oligo-dT primer that incorporated a T7 promoter sequence. The cDNA was then used as a template for in vitro transcription using T7 RNA polymerase and Cy-3-labeled CTP. Labeled cRNA samples were used for hybridization to Agilent 4x 44K microarrays and scanned using an Agilent Scanner. Microarray expression levels were compared to sense transcript tag levels for corresponding genes among all five samples analyzed. All genes that were expressed at a minimum level of at least five tags in any ASSAGE library were assessed. The average correlation coefficient between transcript profiles assessed by microarray and ASSAGE was 0.67. None of 100,000 simulations between microarray expression levels and ASSAGE expression levels of the same genes, randomly shuffled between the five analyzed samples, resulted in average correlation coefficients >0.67 (the maximal average value observed in any of the 100,000 simulations was 0.28).

RT-PCR Detection of Sense and Antisense Transcripts

To validate sense and antisense transcripts identified by ASSAGE, total RNA (1-2 ug) conversion by bisulfite treatment and RNA cleanup was performed as described above. Converted RNA (750 to 1500 ng) was resuspended in ~15 ul of water. A standard first-strand cDNA synthesis was performed by using a random octamer (H)7A/C/T mix and Superscript III reverse transcriptase. Primers used for RT-PCR were: for gene ENSG00000206028 antisense transcript: forward primer—GGTTTAAGGTAGGGGATG-GTTT (SEQ ID NO: 1) (matched to converted sequence of GGTCTAAGGCAGGGGATGGCCC (SEQ ID NO: 2) at chr22: 25398333-25398354) and reverse primer—TCCA-CACTCACATCCCAAAA (SEQ ID NO: 3) (matched to converted sequence of CTCTGGGACGTGAGTGTGGA (SEQ ID NO: 4) at chr22: 25398479-25398498); for gene ENSG00000159496 antisense transcript: forward primer—TTTGGAAAGATGATTGTTGTGG (SEQ ID NO: 5) (matched to converted sequence of TCCGGAAAGATGAC-CGTTGCGG (SEQ ID NO: 6) at chr22: 22364583-22364604) and reverse primer—CAAAACCACA-CAAAAATACCCTAA (SEQ ID NO: 7) (matched to converted sequence of CCAGGGCACCCCTGCGTGGT-TCTG (SEQ ID NO: 8) at chr22: 22364443-22364466); for gene ENSG00000162576 sense transcript: pair #1 forward primer—TGGATGTGGGGTTGTATATTTG (SEQ ID NO: 9) (matched to converted sequence of CGGACGCGGGGCTGTACACCTG (SEQ ID NO: 10) at chr 1: 1280555-1280576) and reverse primer—CACCAC-CAACACCTCCTTCT (SEQ ID NO: 11) (matched to converted sequence of AGAAGGAGGTGCTGGCGGTG (SEQ ID NO: 12) at chr 1: 1280346-1280365); pair #2 forward primer: TTGGTTGTTTGTTTGGAGGTTA (SEQ ID NO: 13) (matched to converted sequence of CTGGCCGTCCGC-CTGGAGGTCA (SEQ ID NO: 14) at chr 1: 1280496-1280517) and reverse primer—CCAATCCCAATACAC-CACCT (SEQ ID NO: 15) (matched to converted sequence of AGGTGGTGCACTGGGACCGG (SEQ ID NO: 16) at chr 1: 1280247-1280266); antisense transcript: pair #1 forward primer—TTGTGGGTGGTTAGGAGGAT (SEQ ID NO: 17) (matched to converted sequence of CTGCGGGCG-GCCAGGAGGAC (SEQ ID NO: 18) at chr 1: 1279608-1279627) and reverse primer—CCCACAAACCCCA-CACTAAC (SEQ ID NO:19) (matched to converted sequence of GCCAGTGTGGGGTCTGCGGG (SEQ ID NO: 20) at chr 1: 1279740-1279759); pair #2 forward primer: GGAGGAAGTTGTGTGTGAGTTTT (SEQ ID NO: 21) (matched to converted sequence of GGAG-GAAGCCGCGCGTGAGCCTT (SEQ ID NO: 22) at chr 1: 1280600-1280622) and reverse primer—CCTCAACCT-TCAACAACAACAA (SEQ ID NO: 23) (matched to converted sequence of TTGCCGTCGTCGAAGGCCGAGG (SEQ ID NO: 24) at chr 1: 1280713-1280734). Forward or reverse oligo in each pair of primer was attached with M13-forward sequencing primer—GTAAAACGACGGC-CAGT (SEQ ID NO: 25) to facilitate the sequencing of each RT-PCR product.

All primers were synthesized by Invitrogen. RT-PCR for converted RNA was performed in 20 ul reactions containing 1×PCR buffer (67 mM Tris-HCT, pH 8.8, 6.7 mM $MgCl_2$, 16.6 mM NH4SO4, 10 mM 2-mercaptoethanol), 0.5 mM dNTPs, 0.5 uM forward and 0.5 uM reverse primers, 5% DMSO and 1 u Platinum Taq (Invitrogen), and cDNA generated from 0.4-4 ng of total RNA. PCR reactions were carried out using a touchdown PCR protocol (1 cycle of 94° C. for 2 min; 3 cycles of 94° C. for 10 sec, 64° C. for 15 sec, 70° C. for 15 sec; 3 cycles of 94° C. for 10 sec, 62° C. for 15 sec, 70° C. for 15 sec; 3 cycles of 94° C. for 10 sec, 60° C. for 15 sec, 70° C. for 15 sec; 41 (for gene ENSG00000206028 and ENSG00000159496 in PBMC) or 33 cycles (for gene ENSG00000162576 in MiaPaCa2 and MRC5) of 94° C. for 10 sec, 58° C. for 15 sec, 70° C. for 15 sec). RT-PCR products were gel-purified by QIAquick gel purification kit (Qiagen) and sequenced using conventional Sanger dideoxy terminators.

Analysis of Antisense Transcript Splicing

To investigate if splicing occurred in the antisense transcripts, total RNA without conversion were first used for RT-PCR (selecting genes that had many antisense tags and no sense tags in the ASSAGE libraries). Briefly, reverse transcription was performed using SuperScript VILO cDNA synthesis kit (Invitrogen) and first strand cDNA was directly used for PCR. To investigate the splicing of antisense transcripts for gene ENSG00000162576 (in MiaPaCa2 cell line), the RT-PCR primers used were: ENSG00000162576 forward primer—GTGCAGGCCACAGTAATGGT (SEQ ID NO: 26) (chr 1: 1280028-1280047) and reverse primer—CTTCGACGACGGCAACTT (SEQ ID NO: 27) (chr 1: 1280708-1280727); RT-PCR products were sequenced to confirm the expected splice event. Second, bisulfate-treated RNA-derived RT-PCR was performed with two primer pairs that matched to converted antisense transcripts and each PCR product was sequenced to confirm that the splicing event was in the expected antisense strand. The primers used were: pair#1 forward primer TGTGTGGTTGT-GTGGGATTT (SEQ ID NO: 28) (matched to converted sequence of CGCGCGGTCGTGCGGGACCC (SEQ ID NO: 29) at chr 1: 1280217-1280236) and reverse primer—CCACCTCTACAAAAACCTAACCAT (SEQ ID NO: 30) (matched to converted sequence of ACGGCCAG-GCTCTCGTAGAGGTGG (SEQ ID NO: 31) of at chr 1: 1280510-1280533); pair #2 forward primer—TTTGGGTG-GTTGTTGGTTTT (SEQ ID NO: 32) (matched to converted sequence of CCCGGGCGGCTGCCGGTCCC (SEQ ID NO: 33) at chr 1: 1280235-1280254) and reverse primer—AAACTCACACACAACTTCCTCCT (SEQ ID NO: 34) (matched to converted sequence of AGGAGGAAGC-CGCGCGTGAGCCT (SEQ ID NO: 35) of at chr 1: 1280599-1280621).

Another approach to identify spliced antisense transcript was to examine the distances between tag1 and tag2 in the PE-ASSAGE antisense tags from Jurkat and MRC5 cells. Using a minimal distance of 600 bp cutoff, we identified 79 and 86 genes as potentially spliced antisense transcripts from Jurkat and MRC5 cells, respectively. We selected six genes (three from each cell line) for RT-PCR screening and four of them generated products; each of the products was ~200 bp in size. These four genes were ENSG00000157483, ENSG00000198624, ENSG00000105679 from Jurkat cells; and ENSG00000121454 from MRC5 cells. Primers used for these four genes' RT-PCR were: for gene ENSG00000157483's antisense transcript: forward primer—AGACCACAAGGAGGAGAAGC (SEQ ID NO: 36; chr 15: 57238352-57238371) and reverse primer—GCTTTCTTCAGAATGGAACATTT (SEQ ID NO: 37; chr 15: 57240413-57240435); for gene ENSG00000198624's antisense transcript: primer pair#1 forward primer—TTCCTGAGTCAACGGAAACTT (SEQ ID NO: 38) (chr 5: 150571883-150571903) and reverse primer—CTGTAGATGACACGCCAGCA (SEQ ID NO: 39) (chr 5: 150572535-150572554); primer pair #2 forward primer—TGCTGGCGTGTCATCTACA (SEQ ID NO: 40) (chr 5: 150572535-150572554) and reverse primer—CGGGGGTTAAAGGCTGATA (SEQ ID NO: 41) (chr 5: 150583287-150583306); for gene ENSG00000105679's antisense transcript: forward primer—GTTGCTGAAACAGCCAAGGT (SEQ ID NO: 42) (chr 19: 40725671-40725690) and reverse primer—CACAGTCACAGAGTCCACGTC (SEQ ID NO: 43) (chr 19: 40724701-40724721); for gene ENSG00000121454's antisense transcript: forward primer—CAGGCCAAGGAGAAAAACAA (SEQ ID NO: 44) (chr 1: 178509749-178509768) and reverse primer: CTAGAGGGCAGCCTCCTCTG (SEQ ID NO: 45) (chr 1: 178509024-178509043).

RT-PCR for gene ENSG00000162576 was performed in 30 ul reactions containing the same components described above. PCR reactions were carried out using a standard PCR protocol (1 cycle of 94° C. for 2 min; 40 cycles of 94° C. for 15 sec, 58° C. for 15 sec, 70° C. for 1 min). RT-PCR for gene ENSG00000157483, ENSG00000198624, ENSG00000105679 and ENSG00000121454 contained all components as described above plus 2 mM ATP. PCR reactions were carried out using a touchdown PCR protocol (1 cycle of 94° C. for 2 min; 3 cycles of 94° C. for 10 sec, 64° C. for 15 sec, 70° C. for 15 sec; 3 cycles of 94° C. for 10 sec, 62° C. for 15 sec, 70° C. for 15 sec; 3 cycles of 94° C. for 10 sec, 60° C. for 15 sec, 70° C. for 15 sec; 36 cycles of 94° C. for 10 sec, 58° C. for 15 sec, 70° C. for 15 sec). All RT-PCR products were sequenced to confirm the occurrence of splicing; comparison with genomic databases showed consensus splice sites at the expected positions of each spliced antisense cDNA fragment.

EXAMPLE 2

We used ASSAGE to study transcription in normal human peripheral blood mononuclear cells (PBMC). Several quality controls were performed to evaluate the library of tags derived from this RNA source. First, we calculated the bisulfite conversion efficiency from the sequences of the tags and found that 95% of the C residues in the original RNA had been converted to U residues (19). Second, we determined whether the bisulfite treatment altered the distribution of tags by preparing libraries without bisulfite treatment. We found a good correlation between the number of sense tags in a gene derived from ASSAGE data and the number of tags derived from RNA-seq data from the same cells ($R2=0.59$). We also found a correlation between the relative expression levels determined by ASSAGE and those assessed by hybridization to microarrays ($R2=0.45$; (19)).

From the PBMC tag library, four million experimental tags could be unambiguously assigned to a specific genomic position in the converted genome. Of the 4 million tags, 47.5% had the sequence of the Plus-strand, meaning that the template of these transcripts had been the Minus-strand, while 52.5% had the sequence of the Minus-strand. This is consistent with the expected equal distribution of sense transcripts from the two strands (20). 90.3% of the 4 million tags could be assigned to known genes while the remaining tags were in unannotated regions of the genome. The fraction of unannotated tags (9.7%) is consistent with data from other sources indicating that there are likely to be actively transcribed genes in human cells that have not yet been discovered or annotated (6, 21-24). Of the informative tags in annotated regions, 11% were antisense and 89% were sense.

EXAMPLE 3

We next assessed the expression of each gene by counting the total number of tags matching a gene or by counting tags with identical sequence matching a gene only once (distinct tags). On average, there were three total tags for each distinct tag, but this number varied widely and reflected the level of expression of the corresponding transcript. With respect to antisense transcription, genes could be divided into three main classes. S genes were defined as those in which sense tags predominated (≥5:1 ratio of distinct sense:distinct antisense tags). AS genes were defined as those in which antisense tags predominated (≥5:1 ratio of distinct antisense:distinct sense tags). The SAS class included the remaining genes, all of which contained both sense and antisense tags. In PBMC, we identified 329 (2.5%) AS genes, 2061 (15.9%) SAS genes and 10586 (81.6%) S genes among the 12,976 Ensembl genes in which at least five distinct tags were observed (Table 1). There were 6,457 genes in which at least two distinct antisense tags were found.

TABLE 1

Classification of genes with respect to antisense tags.

| | Cell type: | | | | | | | | | |
|---|---|---|---|---|---|---|---|---|---|---|
| | PBMC | | Jurkat | | HCT116 | | MiaPaCa2 | | MRC5 | |
| | # of genes | Fraction | # of genes | Fraction | # of genes | Fraction | # of genes | Fraction | # of genes | Fraction |
| All genes | | | | | | | | | | |
| S genes | 10586 | 81.60% | 9928 | 89.60% | 11176 | 88.00% | 9500 | 89.50% | 10165 | 89.30% |
| AS genes | 329 | 2.50% | 240 | 2.20% | 203 | 1.60% | 155 | 1.50% | 212 | 1.9% |
| SAS genes | 2061 | 15.9% | 908 | 8.2% | 1327 | 10.4% | 959 | 9% | 1002 | 8.8% |
| Total | 12976 | | 11076 | | 12706 | | 10614 | | 11379 | |

TABLE 1-continued

Classification of genes with respect to antisense tags.

| | Cell type: | | | | | | | | | |
|---|---|---|---|---|---|---|---|---|---|---|
| | PBMC | | Jurkat | | HCT116 | | MiaPaCa2 | | MRC5 | |
| | # of genes | Fraction | # of genes | Fraction | # of genes | Fraction | # of genes | Fraction | # of genes | Fraction |
| Coding genes | | | | | | | | | | |
| S genes | 10375 | 81.30% | 9778 | 89.50% | 10770 | 87.60% | 9348 | 89.40% | 10029 | 89.20% |
| AS genes | 325 | 2.50% | 239 | 2.20% | 201 | 1.60% | 154 | 1.50% | 210 | 2% |
| SAS genes | 2055 | 16.1% | 907 | 8.3% | 1325 | 10.8% | 959 | 9.2% | 1000 | 8.9% |
| Total | 12755 | | 10924 | | 12296 | | 10461 | | 11239 | |
| Noncoding genes | | | | | | | | | | |
| S genes | 211 | 95.50% | 150 | 98.70% | 406 | 99.00% | 152 | 99.30% | 136 | 97.10% |
| AS genes | 4 | 1.80% | 1 | 0.70% | 2 | 0.50% | 1 | 0.70% | 2 | 1.4% |
| SAS genes | 6 | 2.7% | 1 | 0.70% | 2 | 0.50% | 0 | 0% | 2 | 1.4% |
| Total | 221 | | 152 | | 410 | | 153 | | 140 | |

Table 1 - We classified only those genes whose sum of distinct sense and antisense tags was five or more. S genes contained only sense tags or had a sense/antisense tag ratio of five or more; AS genes contained only antisense tags or had a sense/antisense tag ratio of 0.2 or less; SAS genes contained both sense and antisense tags and had a sense/antisense ratio between 0.2 and 5. Samples were derived from the following sources: PBMC, peripheral blood mononuclear cells isolated from a healthy volunteer; Jurkat, a T-cell leukemia line; HCT116, a colorectal cancer cell line; MiaPaCa2, a pancreatic cancer line; MRC5, fibroblast cell line derived from normal lung.

EXAMPLE 4

Figure 2A:
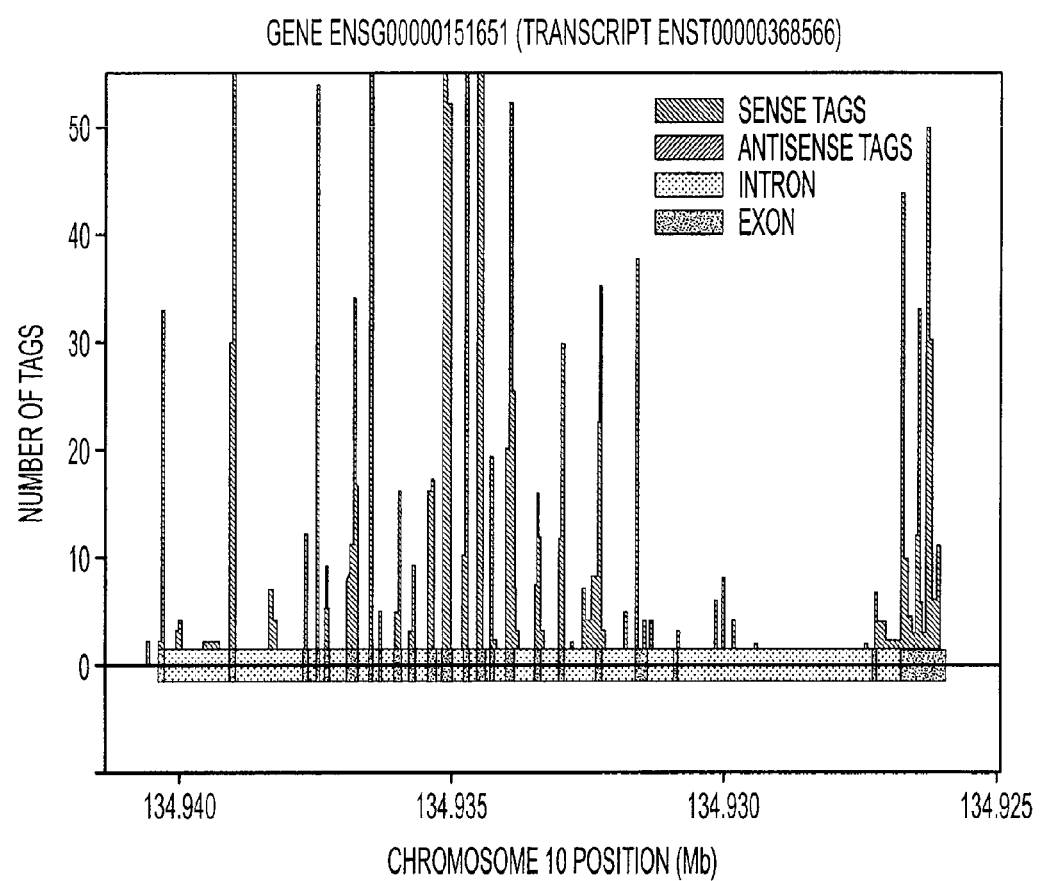
FIG. 2A-2B. Tag distribution in the indicated S (A) and AS (B) genes in PBMC.
Figure 2B:
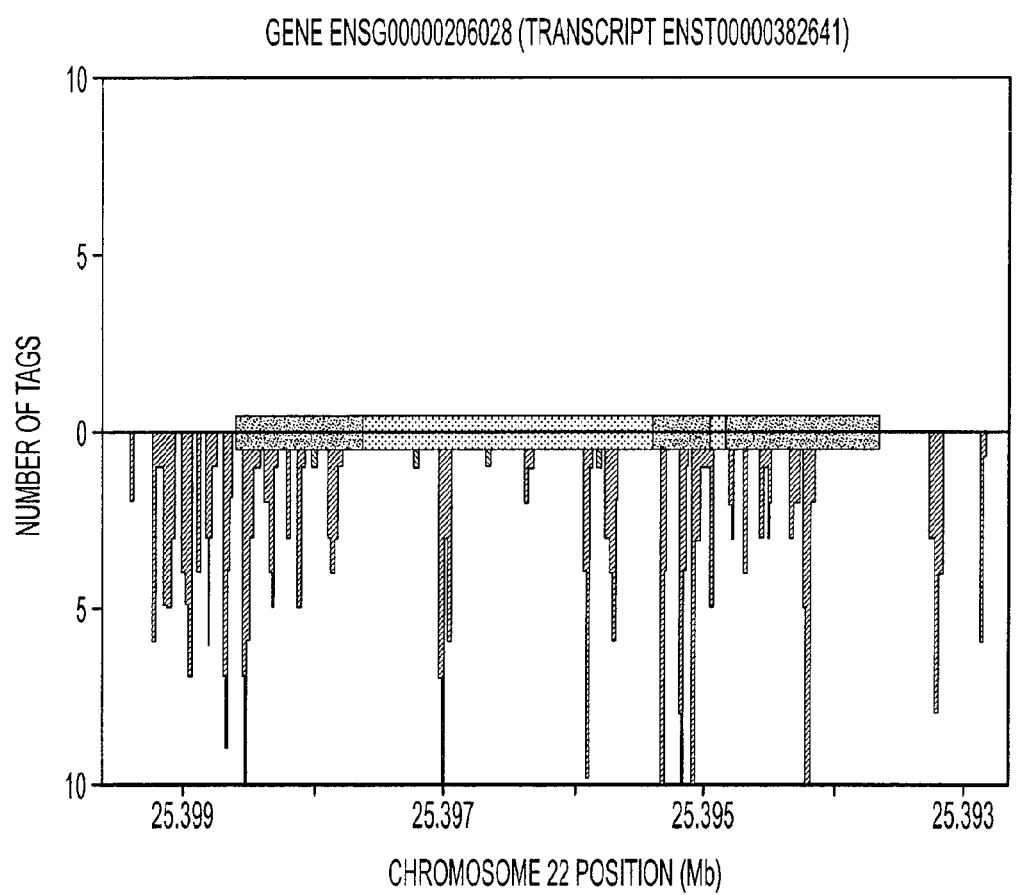
Figure 5A:
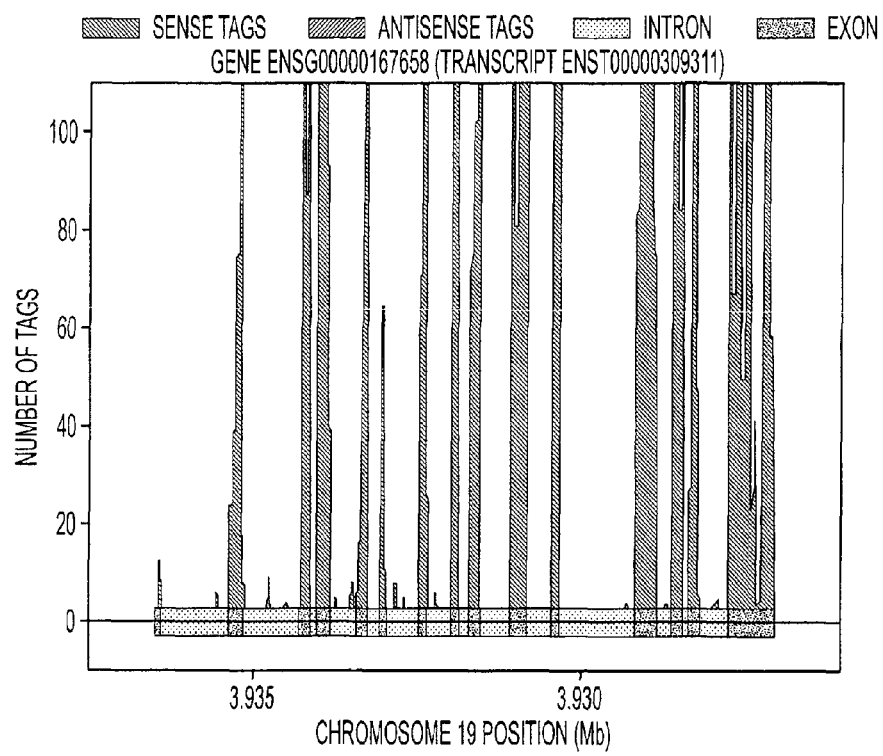
FIG. 5A-5C. Examples of tag distribution in an S gene (A), an AS gene (B) and an S gene with promoter AS tags (C) genes from PBMC.
Figure 5B:
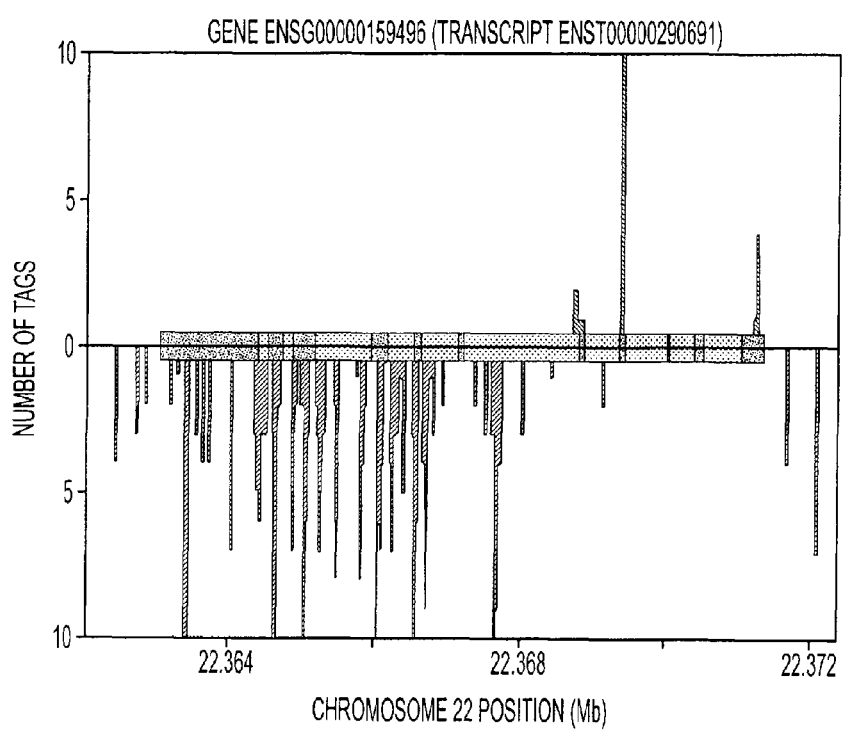
Figure 5C:
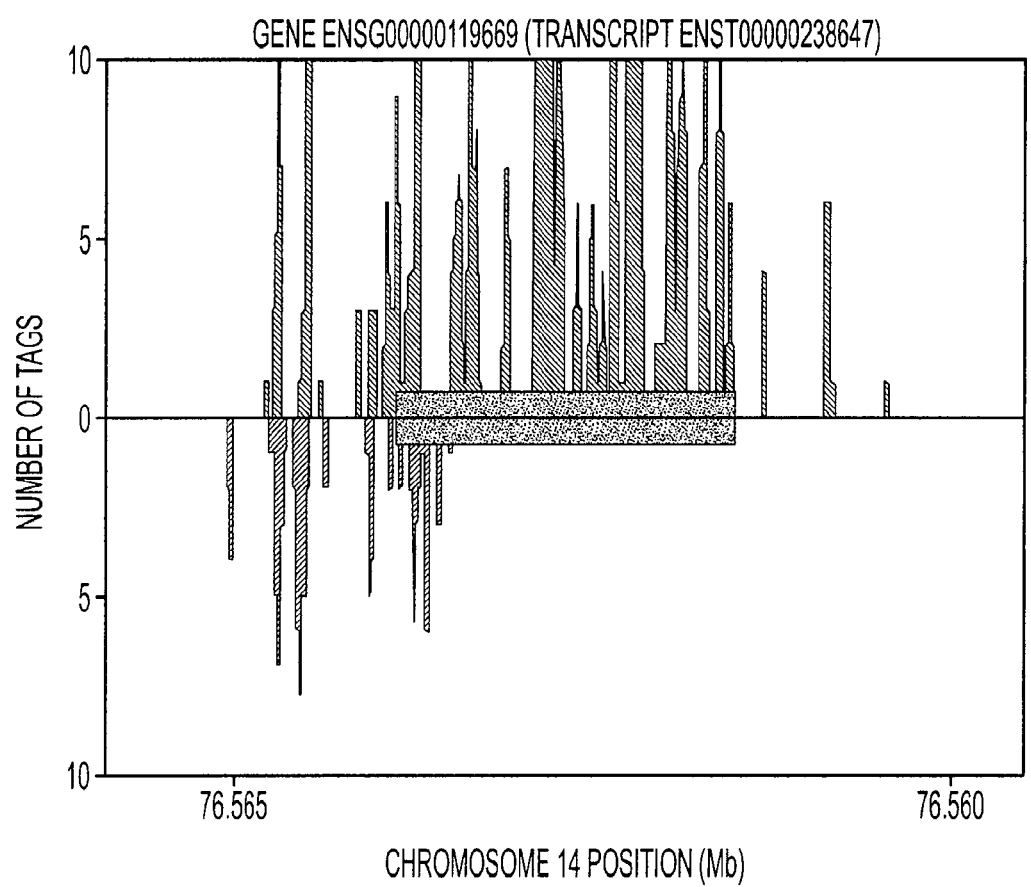
Figure 6:
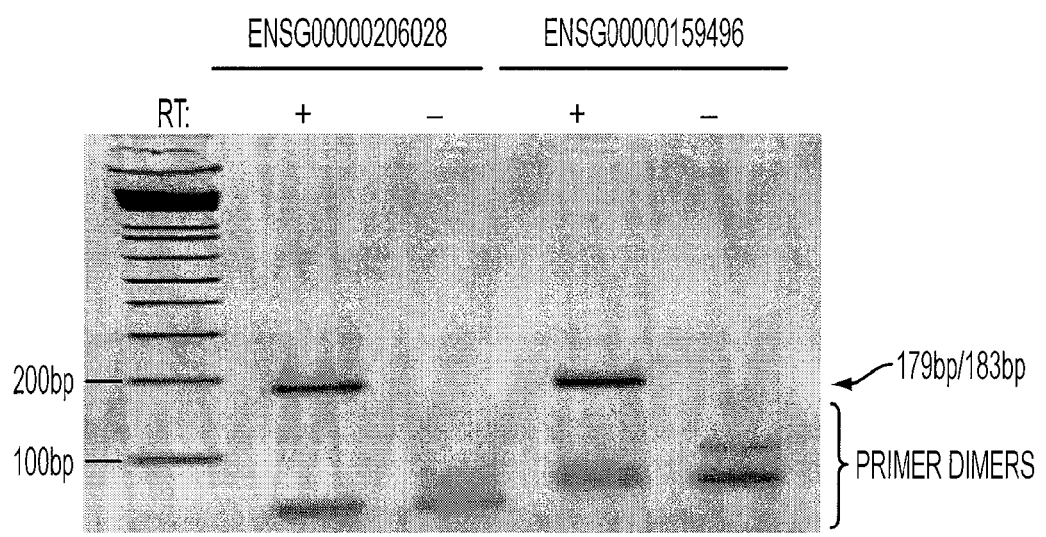
FIG. 6. RT-PCR confirmation of antisense transcripts in PBMC RNA. Bisulfite treated RNA was used as a template for RT-PCR with AS transcript specific primers as described in the Supplementary Materials and Methods. The expected specific products were observed in the reverse transcriptase treated RNA (+ lanes) and not in the minus reverse transcriptase control lanes (− lanes) confirming that the products were derived from RNA.

When normalized by length, there was an obvious concentration of antisense tags in exons compared to the entire genome or to introns (p<0.0001; FIG. 1). Within promoter regions, there was a concentration of antisense tags near the transcription initiation site of the sense transcripts which gradually tapered off upstream (p<0.01; FIGS. 1 and 4). There were also clear differences between the relative distributions of sense and antisense tags, with a higher proportion of antisense tags than sense tags within promoter and terminator regions of genes (p<0.0001; FIG. 1). Examples of the distribution of sense and antisense tags derived from S and AS genes are shown in FIG. 2 and FIG. 5. The prediction of AS transcripts could be confirmed by ASSAGE using gene specific primers (FIG. 6).

EXAMPLE 5

Figure 7A:
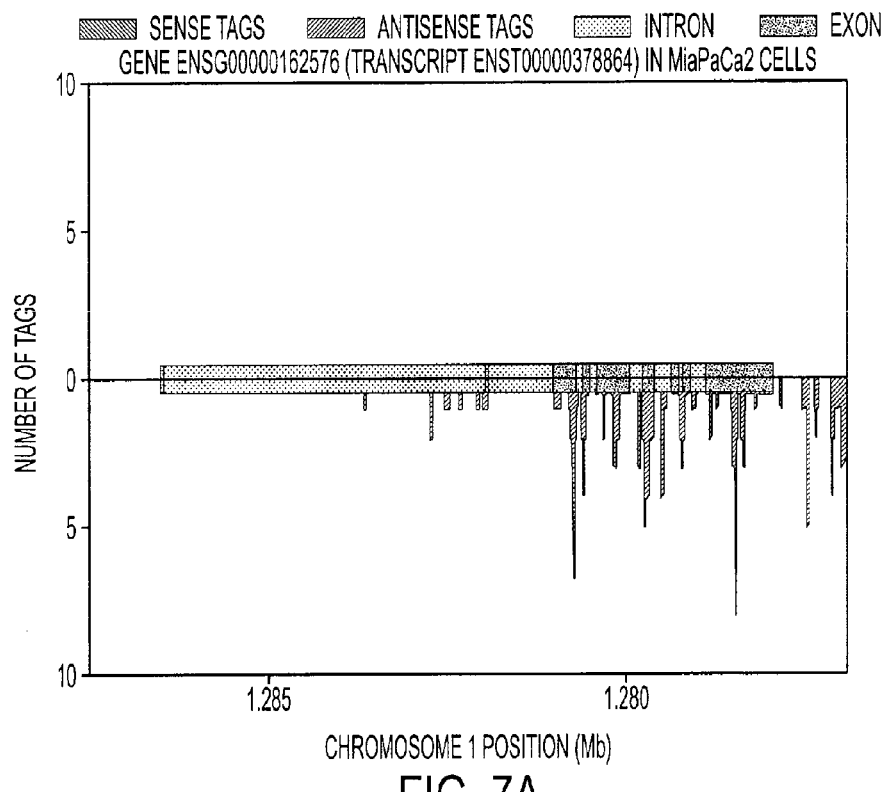
FIG. 7A-7B. Differential regulation of sense and antisense transcripts in different cell types. Gene ENSG00000162576 (transcript ENST00000378864) is an example of a gene that is AS in one cell line (FIG. 7A) and S in another cell line (FIG. 7B).
Figure 7B:
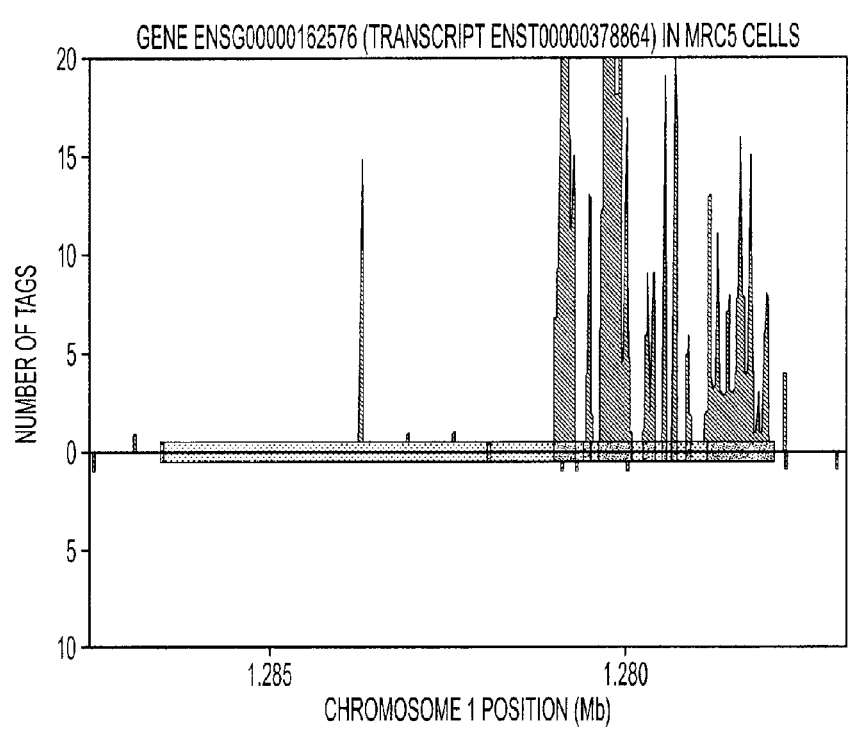
Figure 8A:
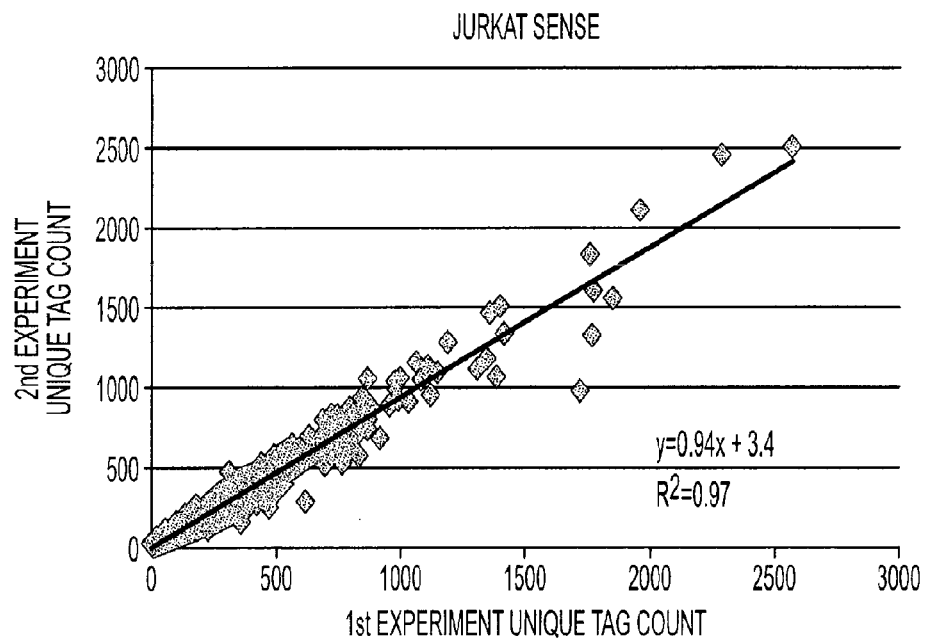
FIG. 8A-8D. Gene expression profiles from two independent ASSAGE experiments. For Jurkat cells, 11076 genes that had a combination of at least 5 unique sense and antisense tags in the first experiment were analyzed (FIG. 8A, FIG. 8B); 11379 genes that met the same selection criteria from MRC5 cells were analyzed (FIG. 8C, FIG. 8D). Each tag count was normalized to one million total tags for plotting.
Figure 8B:
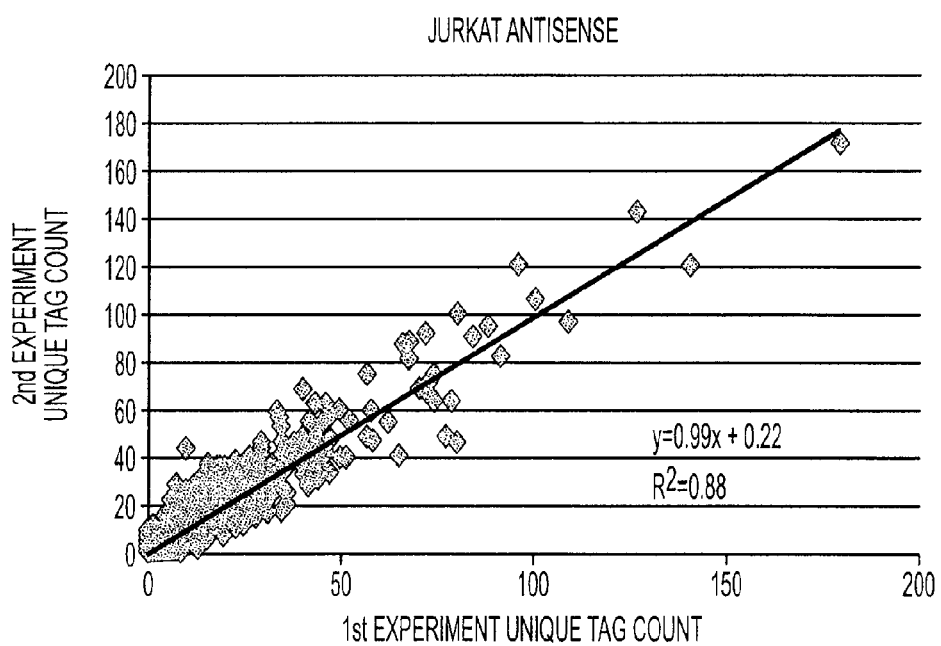
Figure 8C:
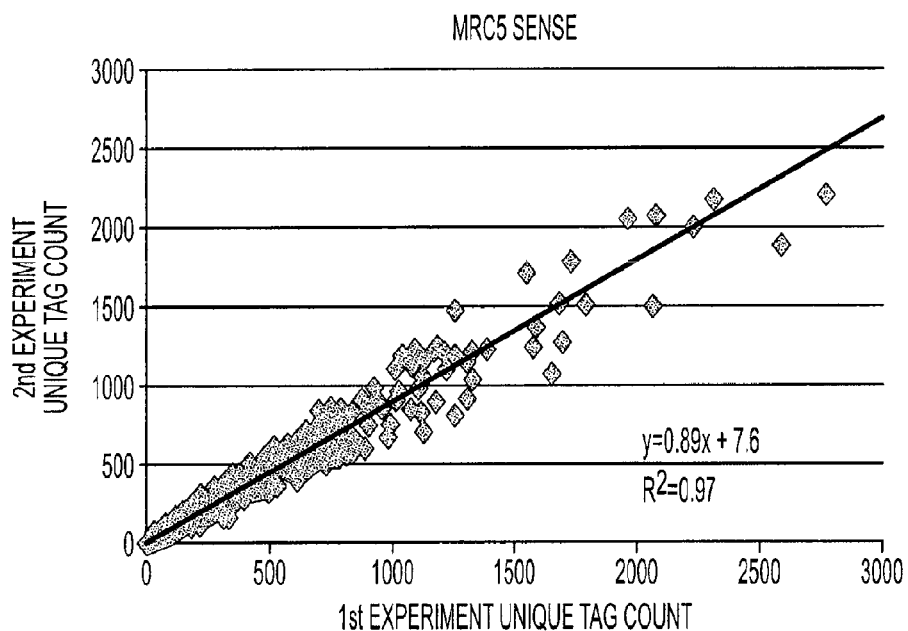
Figure 8D:
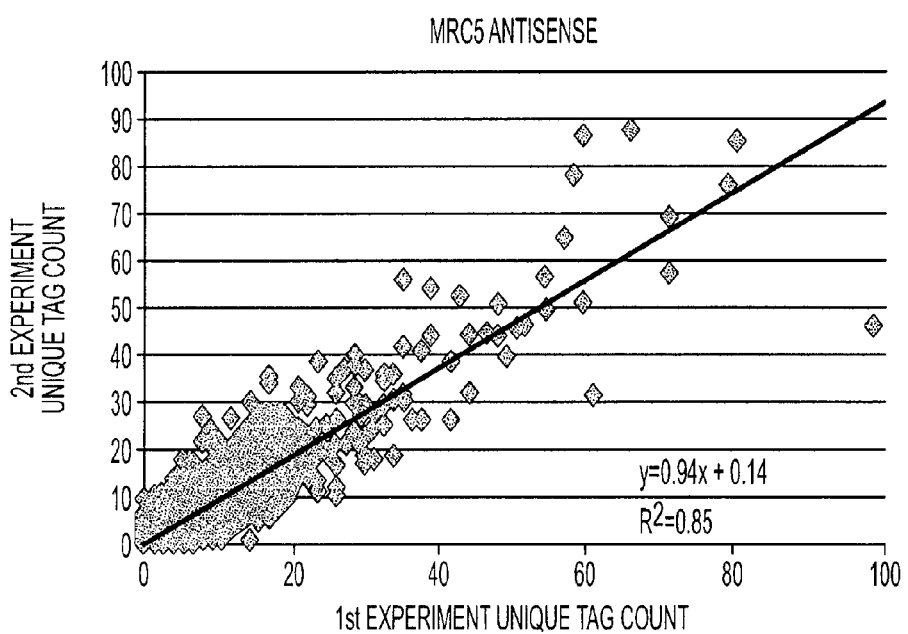
Figure 9A:
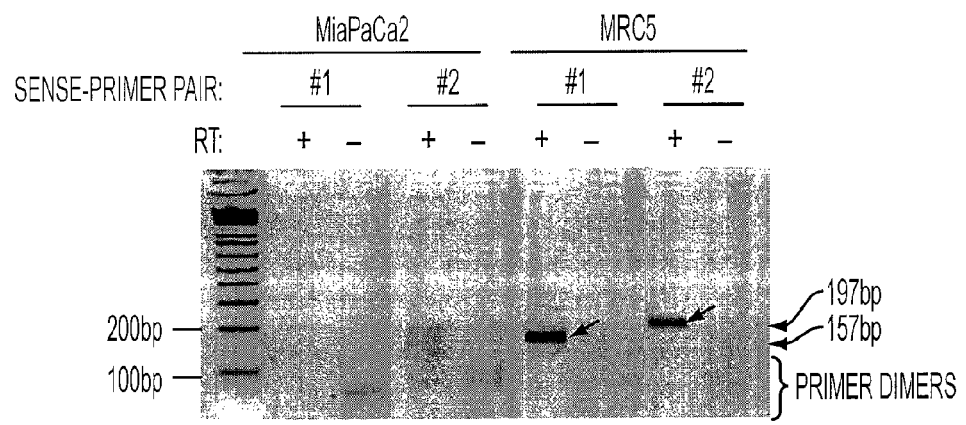
FIG. 9A-9B. Confirmation of differential regulation of sense and antisense transcripts for gene ENSG 00000162576 in different cell types. Bisulfite treated RNA from MiaPaCa2 or MRC5 cells was used as a template for RT-PCR with sense (FIG. 9A) and antisense (FIG. 9B) transcript specific primers as described in the Supplementary Materials and Methods. The expected specific products were observed in the reverse transcriptase treated RNA (+ lanes) and not in the minus reverse transcriptase control lanes (− lanes) confirming that the products were derived from RNA. As predicted by ASSAGE, predominantly sense transcripts were expressed in MRC5 cells and antisense transcripts in MiaCaPa2 cells.
Figure 9B:
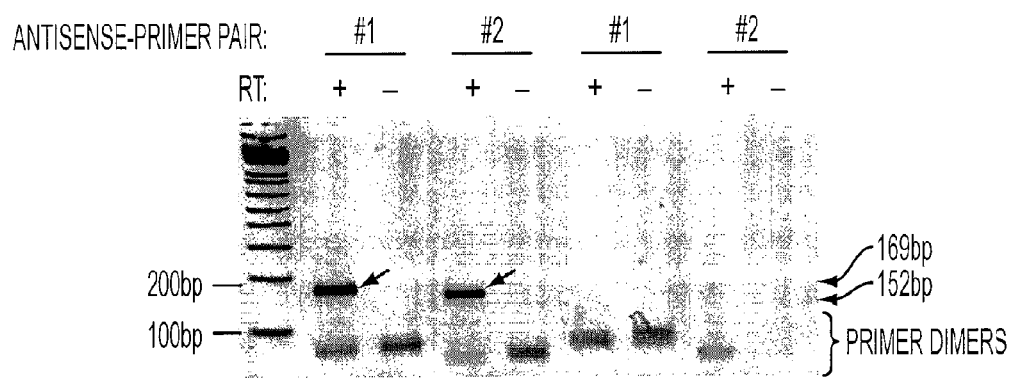
Figure 10A:
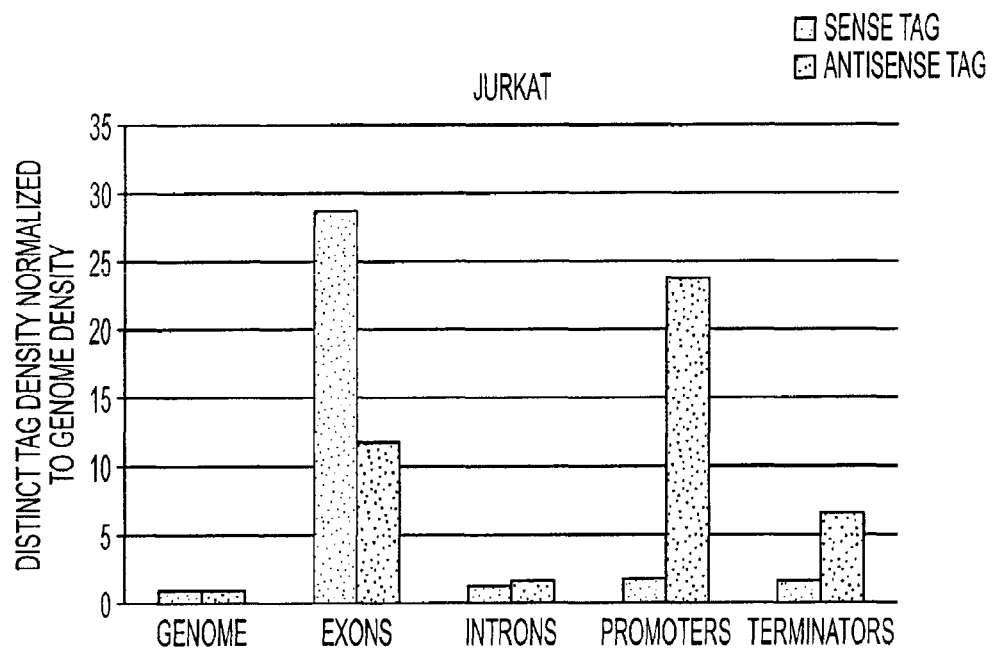
FIG. 10A-10D. ASSAGE tag densities in indicated cell lines. The density of distinct sense and antisense tags in the indicated regions were normalized to the overall genome tag density. The promoter and terminator regions were defined as the 1 kb of sequence that were upstream or downstream, respectively, of the transcript start and end sites.
Figure 10B:
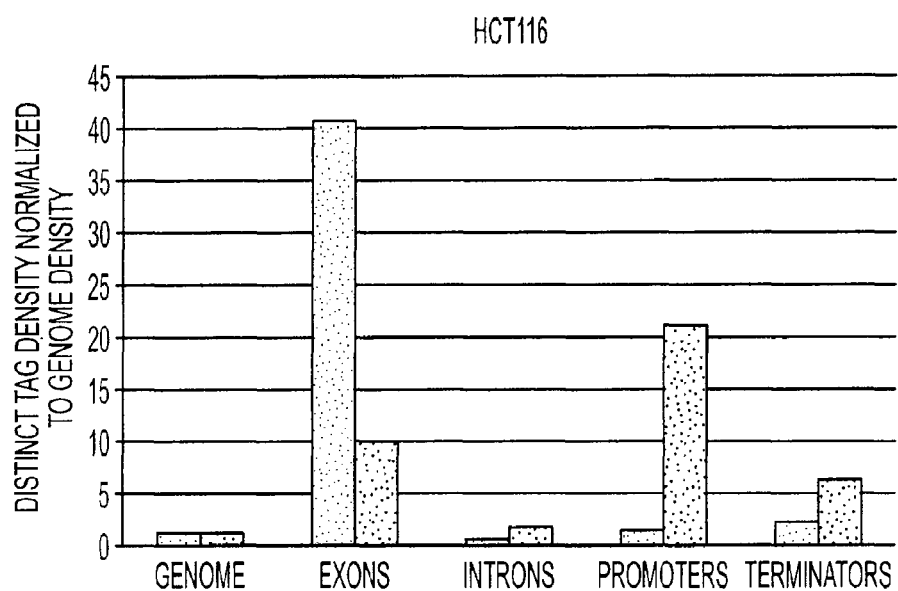
Figure 10C:
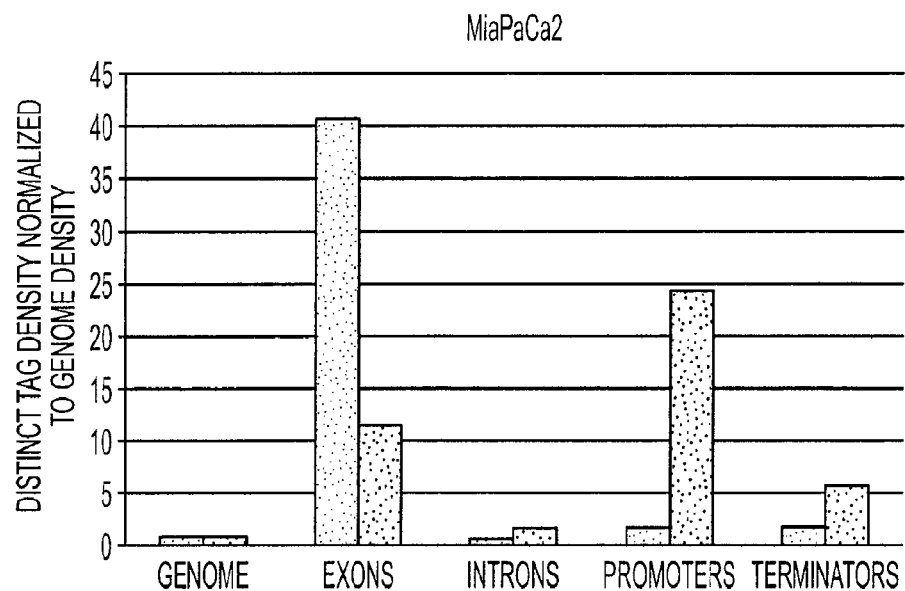
Figure 10D:
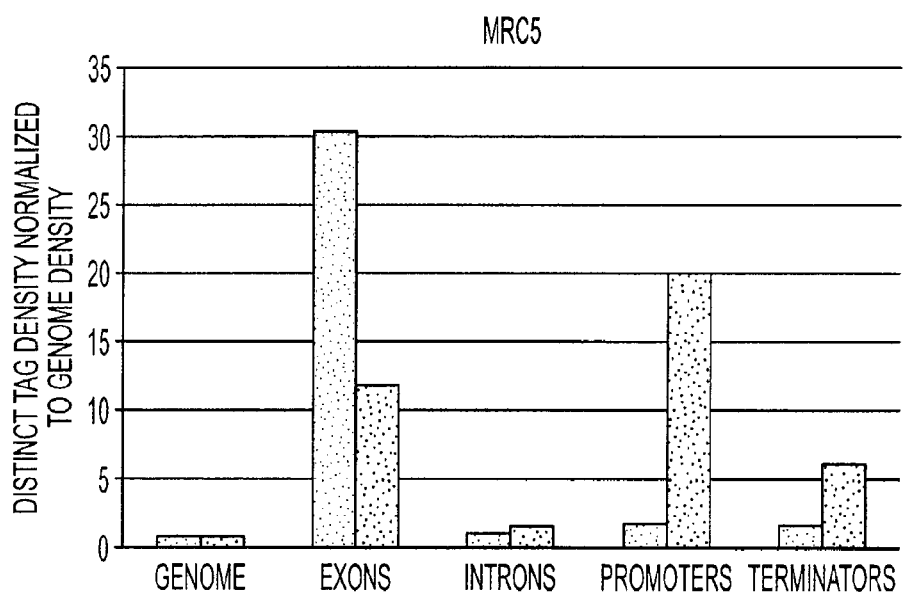
Figure 11A:
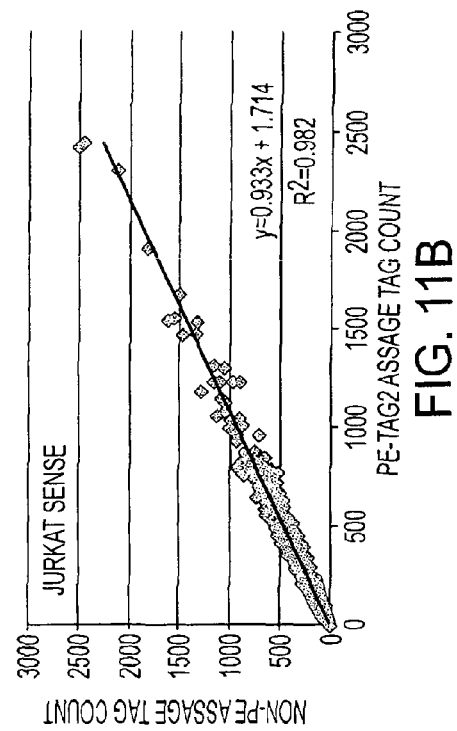
FIG. 11A-11H. Gene expression profiles from paired-end (PE) and regular (non-PE) ASSAGE experiments for Jurkat cell line (FIG. 11A-D) and MRC5 cell line (FIG. 11E-H). Non-PE ASSAGE experiment data was the same dataset as 2nd-experiment data in FIG. 8. Only genes that had at least one unique tag from PE or non-PE experiment were included in each analysis. Each tag count was normalized to one million total tags for plotting.
Figure 11C:
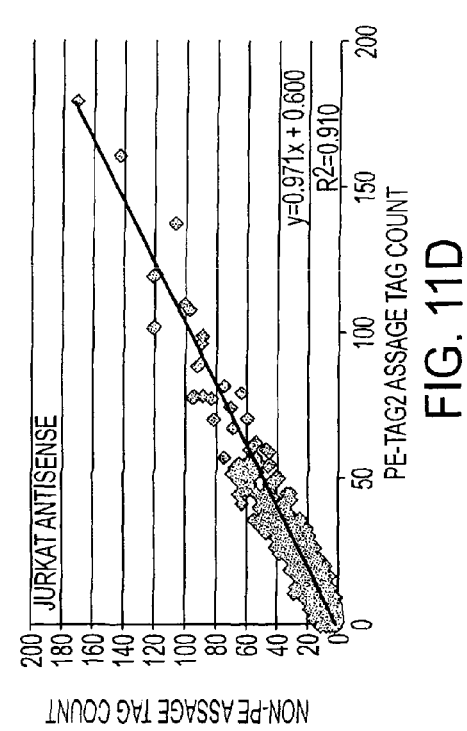
Figure 11B:
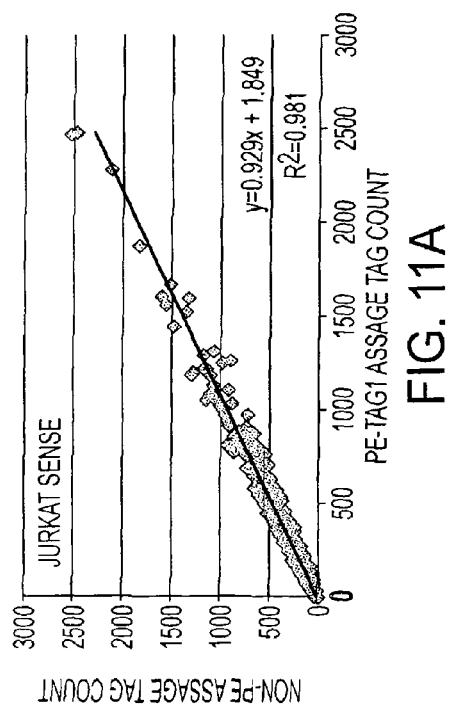
Figure 11D:
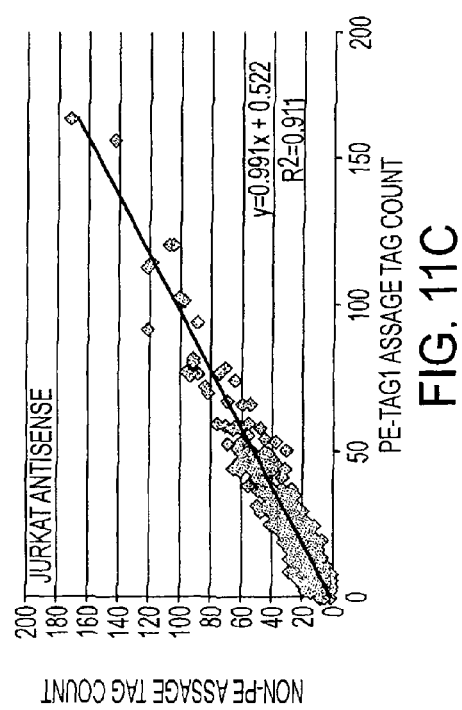
Figure 11E:
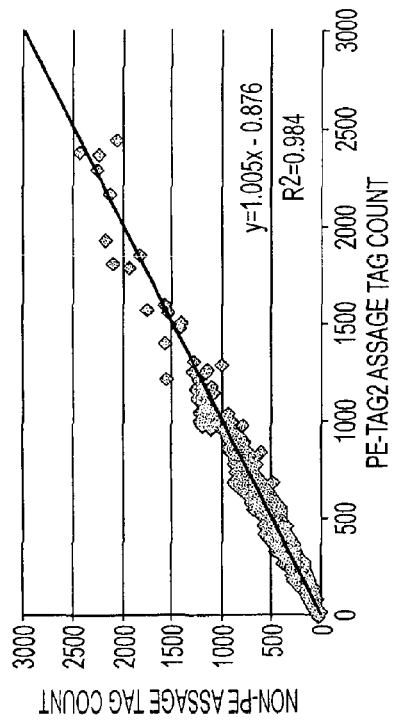
Figure 11F:
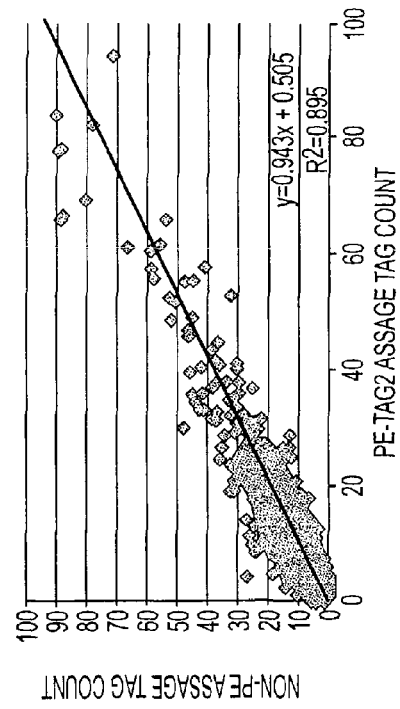
Figure 11G:
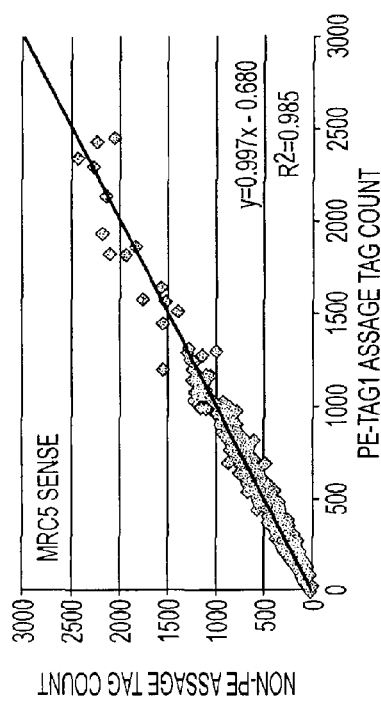
Figure 11H:
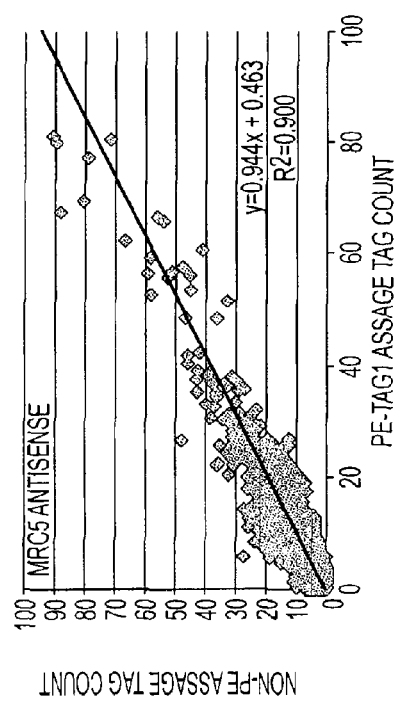

To determine whether the patterns described above were particular to PBMC, we used ASSAGE to study four additional human cell types. In all cases, the patterns observed were similar to those in PBMCs including the proportion of S, AS, and SAS genes found in each of the four lines (Table 1). However, the identity of the S, AS, and SAS genes varied among the cell lines, suggesting that the expression of antisense tags may be regulated in a cell or tissue-specific manner (FIG. 7). These differences were not related to inter-experimental variation as repeat experiments performed with independently generated ASSAGE libraries from the same RNA sample were highly correlated (FIG. 8) and differential expression could be confirmed by strand specific-PCR from RNA (FIG. 9). In every sample, there was a concentration of both sense and antisense tags within exons compared to the whole genome or to intronic regions and a preferential concentration in promoter and terminator regions (p<0.01; FIGS. 4 and 10).

EXAMPLE 6

Figure 12A:
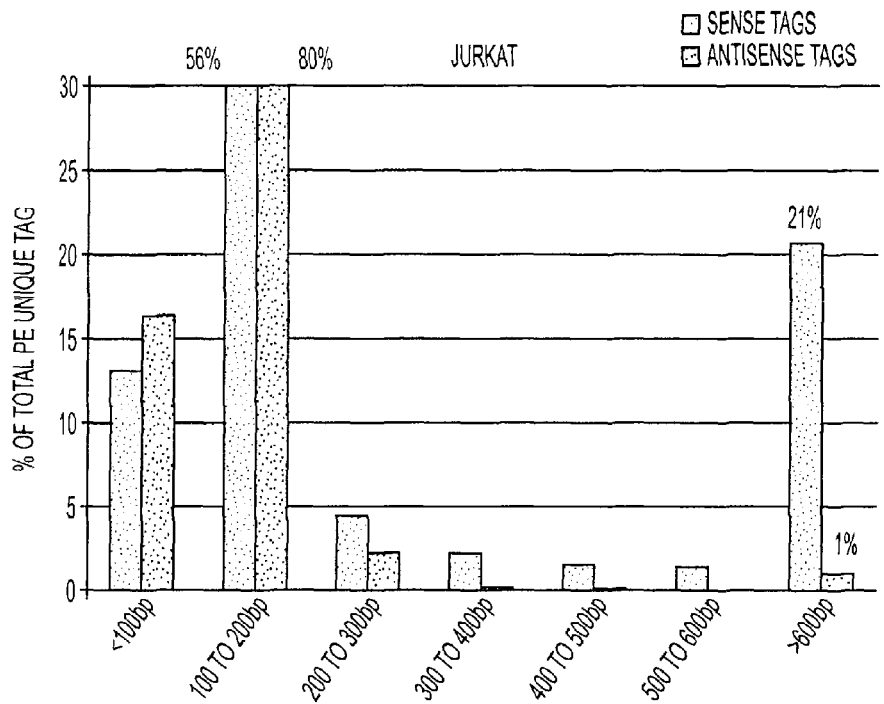
FIG. 12A-12B. Distribution of PE-ASSAGE tags from Jurkat (FIG. 12A) and MRC5 (FIG. 12B) classified by distances between genomic positions of paired tag1 and tag2. Note the percentages of PE tag with tag 1 to tag 2 distances of 100-200 bp or >600 bp are indicated on the top of each bar.
Figure 12B:
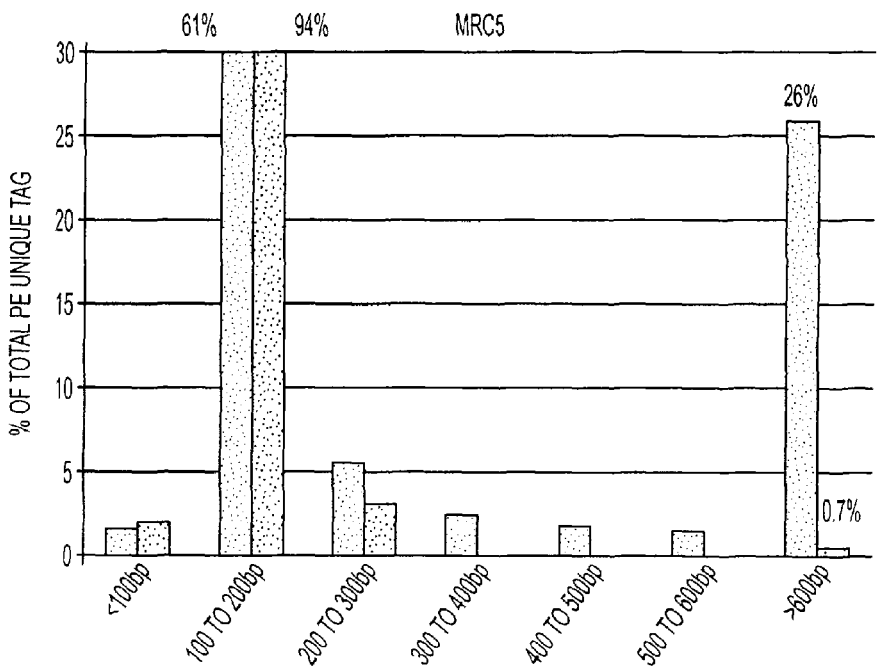
Figure 13A:
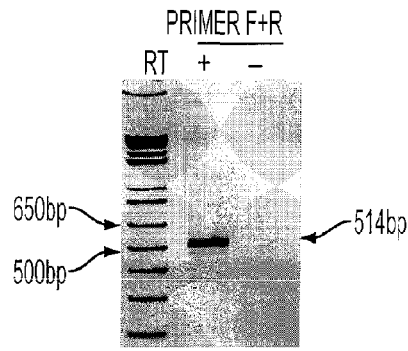
FIG. 13A-13B. An example of splicing of antisense transcript of gene ENSG00000162576 in MiaPaCa2 cells. RT-PCR identified a portion of the transcript that was spliced (FIG. 13A). Sequencing of the isolated PCR product and comparison with genomic sequence revealed that the splice junction was flanked by canonical splice sites on the DNA strand encoding the antisense transcript (FIG. 13B). The splice event was distinct from the known splicing of sense transcript (FIG. 13C). Similar splicing events were confirmed by PCR and sequencing for AS transcripts to genes ENSG00000157483, ENSG00000198624 and ENSG00000105679 from Jurkat cells and to gene ENSG00000121454 from MRC5 cells.
Figure 13B:
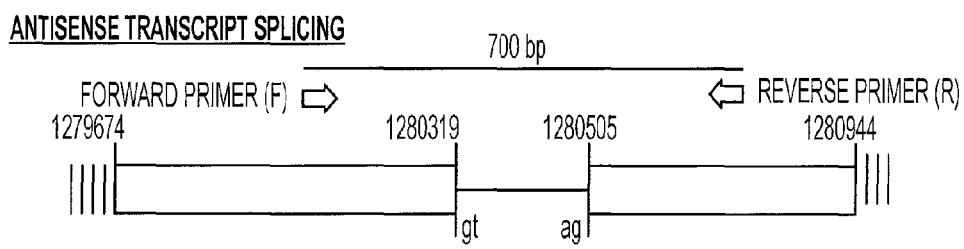
Figure 13C:
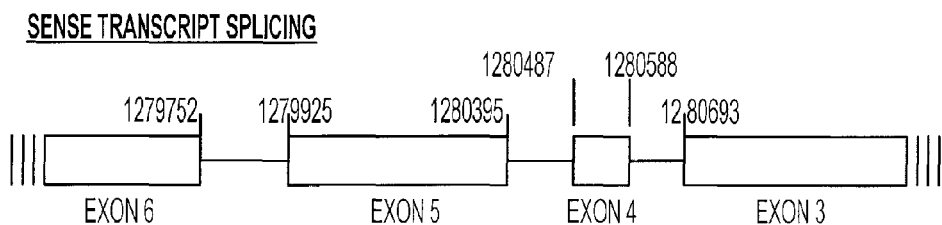
Figure 14A:
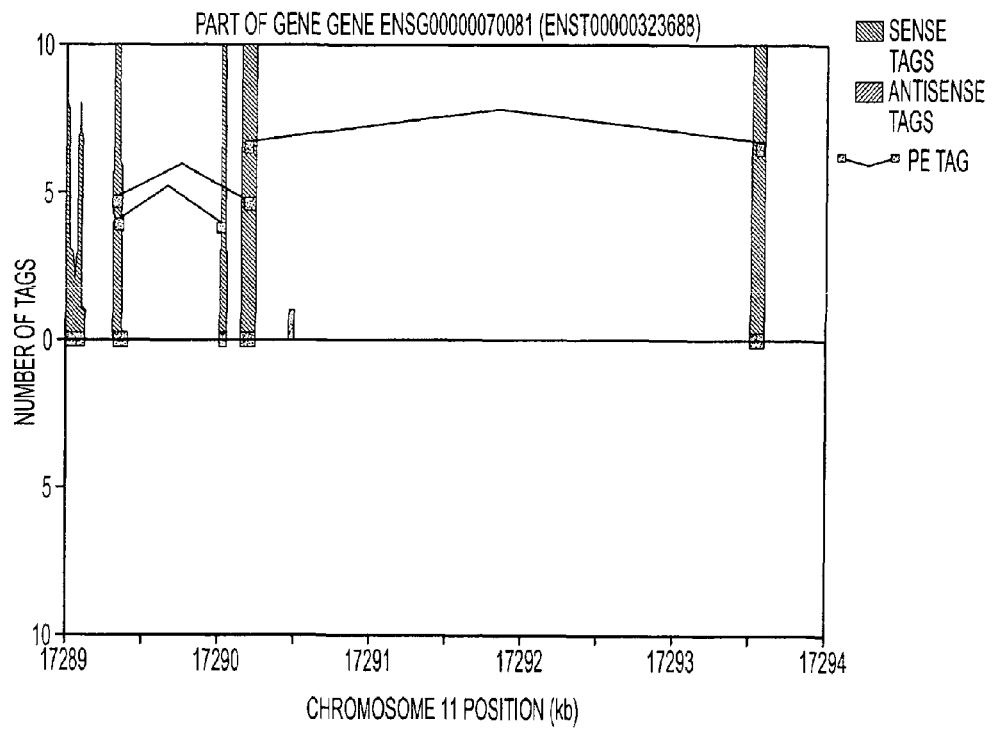
FIG. 14A-14C. Transcript splicing revealed by PE-ASSAGE tag analysis. One example of sense (FIG. 14A) and two of antisense (FIG. 14B, FIG. 14C) transcripts splicing events identified in Jurkat cells are shown. ASSAGE tag data for mapping was from an independent regular ASSAGE experiment (experiment #2). Each pear-end clone illustrated in the map represents one or multiple tags in which distances between tag 1 and tag 2 were greater than 600 bp.
Figure 14B:
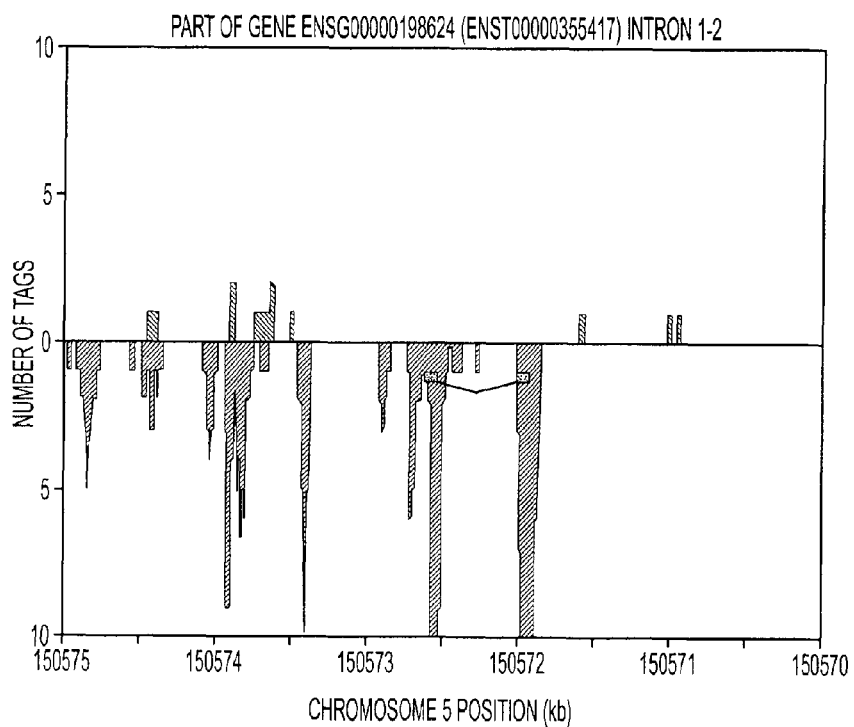
Figure 14C:
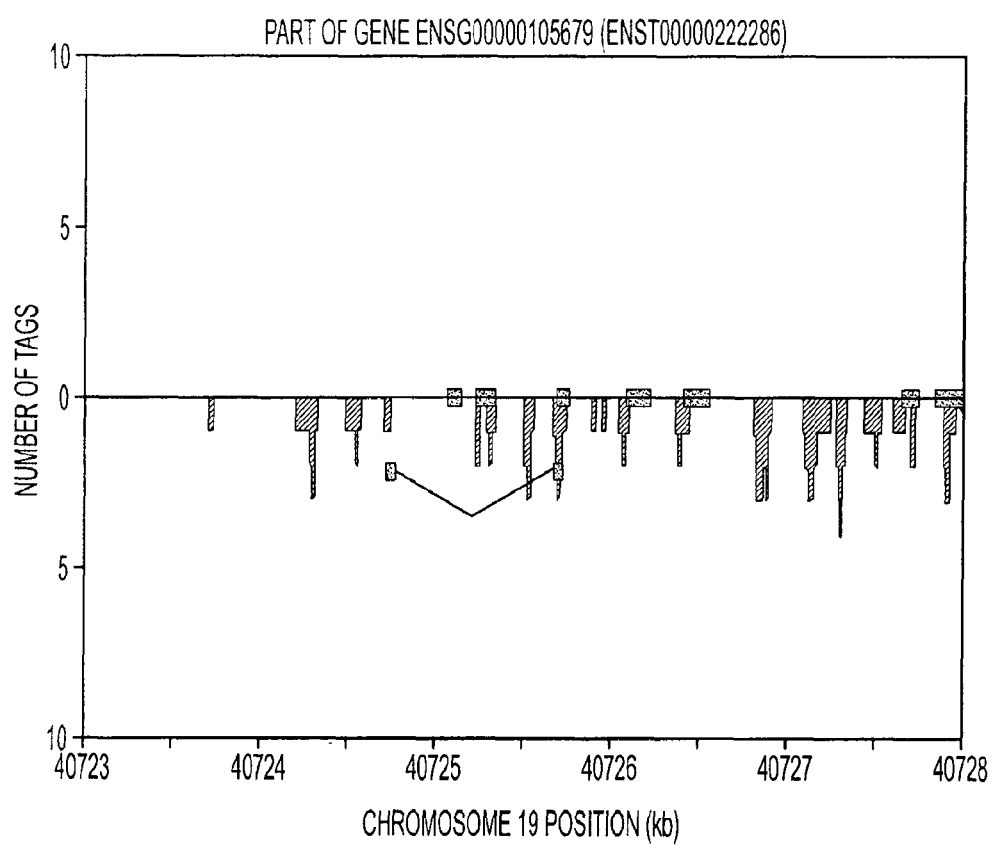
Figure 15A:
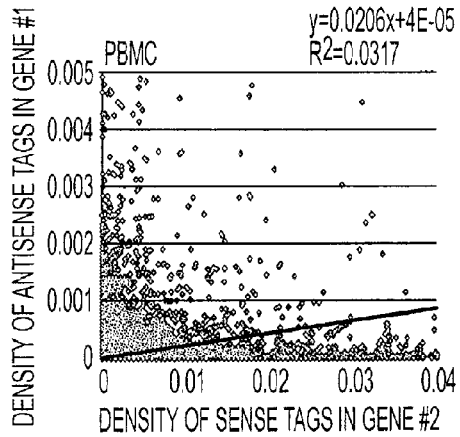
FIG. 15A-15E. Lack of correlation between density of distinct antisense tags of gene #1 and sense tags from gene #2 in the indicated cell lines. Gene #2 is defined as the closest neighboring gene arranged tail-to-tail with gene #1. A total of 28,269 genes were evaluated in each cell sample.
Figure 15B:
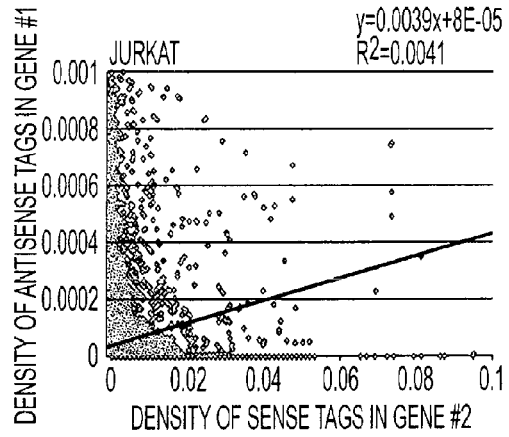
Figure 15C:
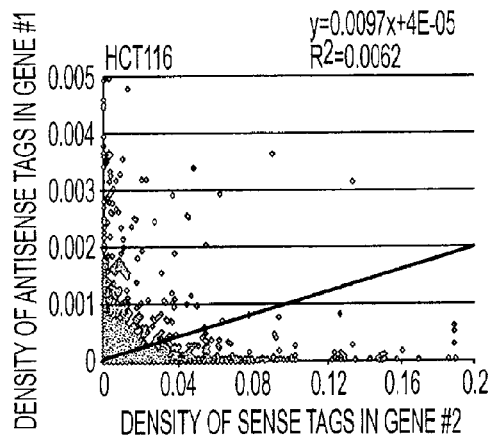
Figure 15D:
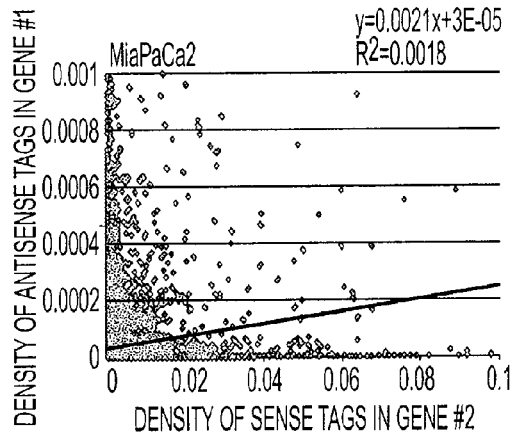
Figure 15E:
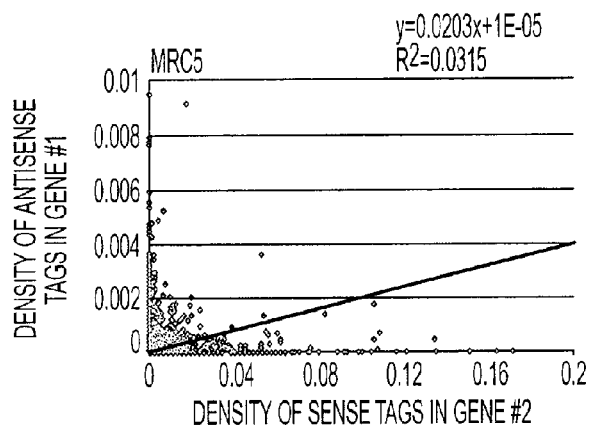

To determine whether splicing of antisense transcripts occurred, we constructed new libraries from Jurkat and MRC5 cells and determined the sequences of both ends of each cDNA fragment ("paired-end sequencing"). As expected, transcripts levels assessed with this paired-end ASSAGE and the original ASSAGE were highly correlated (FIG. 11). The size-selected transcript fragments used to construct these libraries were, on average, ~175 bp in length. A cDNA fragment whose ends were located at genomic positions more than three times this distance (>600 bp apart) would be expected to represent spliced transcripts. By this criterion, more than 20% of sense strand cDNA fragments were spliced (FIG. 12). In contrast, only ~1% of antisense fragments exhibited this spliced pattern. Sequencing of five putative spliced antisense transcripts confirmed the splicing and comparison with genomic DNA revealed the splice site consensus sequences at the expected locations FIGS. 13 and 14).

REFERENCES

The disclosure of each reference cited is expressly incorporated herein.

1. P. O. Brown, D. Botstein, *Nat Genet.* 21, 33 (1999).
2. V. E. Velculescu et al., *Cell* 88, 243 (1997).
3. M. Lapidot, Y. Pilpel, *EMBO Rep* 7, 1216 (2006).
4. A. Mazo, J. W. Hodgson, S. Petruk, Y. Sedkov, H. W. Brock, *J Cell Sci* 120, 2755 (2007).
5. J. A. Timmons, L. Good, *Biochem Soc Trans* 34, 1148 (2006).
6. P. Kapranov, A. T. Willingham, T. R. Gingeras, *Nat Rev Genet.* 8, 413 (2007).
7. O. Yazgan, J. E. Krebs, *Biochem Cell Biol* 85, 484 (2007).
8. J. Chen et al., *Nucleic Acids Res* 32, 4812 (2004).
9. M. E. Fahey, T. F. Moore, D. G. Higgins, *Comp Funct Genomics* 3, 244 (2002).
10. B. Lehner, G. Williams, R. D. Campbell, C. M. Sanderson, *Trends Genet.* 18, 63 (2002).
11. J. Shendure, G. M. Church, *Genome Biol* 3, RESEARCH0044 (2002).
12. R. Yelin et al., *Nat Biotechnol* 21, 379 (2003).
13. H. Kiyosawa, I. Yamanaka, N. Osato, S. Kondo, Y. Hayashizaki, *Genome Res* 13, 1324 (2003).
14. D. J. Lipman, *Nucleic Acids Res* 25, 3580 (1997).

15. G. G. Carmichael, *Nat Biotechnol* 21, 371 (2003).
16. S. Katayama et al., *Science* 309, 1564 (2005).
17. Y. Okazaki et al., *Nature* 420, 563 (2002).
18. D. Kampa et al., *Genome Res* 14, 331 (2004).
19. See supporting material on *Science* Online.
20. A. J. Simpson, S. J. de Souza, A. A. Camargo, R. R. Brentani, *Comp Funct Genomics* 2, 169 (2001).
21. B. A. Peters et al., *Genome Res* 17, 287 (2007).
22. M. Sultan et al., *Science* 321, 956 (2008).
23. A. Mortazavi, B. A. Williams, K. McCue, L. Schaeffer, B. Wold, *Nat Methods* 5, 621 (2008).
24. J. Q. Wu et al., *Genome Biol* 9, R3 (2008).
25. J. M. Johnson, S. Edwards, D. Shoemaker, E. E. Schadt, *Trends Genet.* 21, 93 (2005).
26. K. Struhl, *Nat Struct Mol Biol* 14, 103 (2007).
27. He Y, et al., *Science,* 322, 1855 (2008).

We claim:

1. A method, comprising the steps of:

isolating RNA;

treating the isolated RNA with bisulfite to convert Cytosine residues to Uracil residues, thereby forming bisulfite converted RNA;

reverse transcribing the bisulfite converted RNA to form cDNA;

determining nucleotide sequence of at least a portion of said cDNA;

comparing and identifying matches between (a) determined nucleotide sequence data of the cDNA and (b) sequence data of a strand of DNA, wherein the sequence data have been transformed in silico by changing Cytosine residues to Uracil or Thymidine residues; and determining whether a determined nucleotide sequence was transcribed from the strand of DNA based on identified matches.

2. The method of claim 1 wherein the step of treating converts non-quantitatively Cytosine residues to Uracil residues, thereby forming incompletely bisulfite converted RNA.

3. The method of claim 1 wherein the step of treating converts at least 95% of Cytosine residues to Uracil residues.

4. The method of claim 1, wherein:
said RNA is obtained by transcribing two complementary DNA strands;
said reverse transcribing is performed by synthesizing first strand DNA using bisulfite converted RNA as a template for reverse transcription; and
further comprising the steps of:
synthesizing second strand DNA using the first strand DNA as template; and
forming double-stranded DNA molecules from first and second strand DNA.

5. The method of claim 4 wherein the RNA is expressed from one of the two complementary DNA strands in a cell.

6. The method of claim 4 wherein the RNA is synthesized in vitro.

7. The method of claim 5 further comprising the step of removing ribosomal RNA (rRNA) from the expressed RNA to form rRNA-depleted RNA.

8. The method of claim 4 wherein the RNA is treated with bisulfite to convert at least 95% of Cytosine residues to Uracil residues.

9. The method of claim 4 further comprising determining the sequence of a double-stranded DNA molecule and comparing the sequence to a database of genomic sequence that has been transformed in silico by changing Cytosine residues to Uracil or Thymidine residues.

10. A method, comprising the steps of:
isolating RNA;
treating the isolated RNA with bisulfite to convert non-quantitatively Cytosine residues to Uracil residues, thereby forming incompletely bisulfite converted RNA having 95% or less converted Cytosine residues to Uracil residues;
reverse transcribing the incompletely bisulfite converted RNA to form cDNA;
determining nucleotide sequence of at least a portion of said cDNA;
comparing and identifying matches between (a) determined nucleotide sequence data of the cDNA and (b) sequence data of a strand of DNA, wherein the sequence data have been transformed in silico by changing Cytosine residues to Uracil or Thymidine residues; and
determining whether a determined nucleotide sequence was transcribed from the strand of DNA based on identified matches.

11. The method of claim 10 further comprising comparing (a) determined nucleotide sequence data of the cDNA to (c) sequence data of a strand of DNA, wherein the sequence data have been transformed in silico by changing Guanine residues to Adenine residues.

12. The method of claim 10 further comprising the steps of:
determining nucleotide sequence of at least a portion of said cDNA;
comparing and identifying matches or mismatches between (a) determined nucleotide sequence data of the cDNA; and (b) sequence data of a strand of DNA, wherein the sequence data have been transformed in silico by changing Cytosine residues to Uracil or Thymidine residues; (c) sequence data of a strand of DNA, wherein the sequence data have been transformed in silico by changing Guanine residues to Adenine residues; or (d) sequence data of a strand of DNA that has been derived experimentally from a biological source; and
identifying nucleotides which have been converted from Cytosine to Uracil in the RNA or identifying nucleotides which have not been converted from Cytosine to Uracil in the RNA based on the matches or mismatches.

13. The method of claim 10 wherein the isolated RNA is total RNA.

14. The method of claim 10 wherein the isolated RNA is rRNA-depleted RNA.

15. The method of claim 10 wherein the isolated RNA is polyA-selected RNA.

16. The method of claim 10 wherein the isolated RNA is size-selected.

17. The method of claim 10 wherein the isolated RNA is microRNA.

18. The method of claim 10 wherein the incompletely bisulfite converted RNA is reverse transcribed to form a first strand of DNA and the first strand is used as a template to form a second strand of DNA, which together form a double-stranded DNA.

19. The method of claim 10 wherein the RNA is expressed and isolated from a cell sample.

20. The method of claim 10 wherein the sequence data of a strand of DNA is in a database of human genomic sequence.

21. The method of claim 10 wherein the strand of DNA is a sense strand of a gene.

22. The method of claim 10 wherein the strand of DNA is an anti-sense strand of a gene.

23. The method of claim 10 wherein a match is identified when at least 32 out of 36 contiguous nucleic acid bases are identical between (a) and (b).

24. The method of claim 12 wherein a match is identified when at least 32 out of 36 contiguous nucleic acid bases are identical between (a) and (b) or (a) and (c).

25. The method of claim 18 wherein adaptors are ligated to each end of the double-stranded DNA.

26. The method of claim 18 wherein sequence from both ends of a double-stranded DNA molecule is determined.

27. The method of claim 11 further comprising tallying (a) individual determined nucleotide sequences which were transcribed from the strand of DNA separately from (b) individual determined nucleotide sequences transcribed from a strand of DNA which is complementary to the strand.

28. The method of claim 26 wherein sequences from both ends are separately matched to a database of genomic sequence and if the ends are separated in the genomic sequence by a length larger than a length of the double-stranded DNA molecule, identifying the double-stranded DNA molecule as derived from a spliced RNA molecule.

29. The method of claim 26 further comprising the step of determining that the sequences from both ends match to one gene only, match to the same gene, and match to the same strand of the gene in a genome.

30. The method of claim 29 wherein if at least two matched sequences in a bisulfite converted RNA molecule are discontinuous in the genome, identifying the bisulfite converted RNA molecule as a spliced RNA molecule.

31. The method of claim 18 wherein the first strand DNA is reverse transcribed utilizing random hexamers or random octamers as primers.

32. The method of claim 18 wherein the double-stranded DNA is size selected and used as a template for sequencing by synthesis.

33. The method of claim 32 wherein the double-stranded DNA is size-selected for between 120 and 200 bp.

34. The method of claim 18 wherein nucleotide sequence determination is performed using the double-stranded DNA as a template to synthesize DNA molecules.

* * * * *

SEQUENCE LISTING

```
<160> NUMBER OF SEQ ID NOS: 57

<210> SEQ ID NO 1
<211> LENGTH: 22
<212> TYPE: DNA
<213> ORGANISM: Artificial Sequence
<220> FEATURE:
<223> OTHER INFORMATION: bisulfite converted human sequence

<400> SEQUENCE: 1
ggtttaaggt agggatggt tt                                              22

<210> SEQ ID NO 2
<211> LENGTH: 22
<212> TYPE: DNA
<213> ORGANISM: Artificial Sequence
<220> FEATURE:
<223> OTHER INFORMATION: bisulfite converted human sequence

<400> SEQUENCE: 2
ggtctaaggc agggatggc cc                                              22

<210> SEQ ID NO 3
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 3
tccacactca catcccaaaa                                                20

<210> SEQ ID NO 4
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 4
ctctgggacg tgagtgtgga                                                20

<210> SEQ ID NO 5
<211> LENGTH: 22
<212> TYPE: DNA
<213> ORGANISM: Artificial Sequence
<220> FEATURE:
<223> OTHER INFORMATION: bisulfite converted human sequence

<400> SEQUENCE: 5
tttggaaaga tgattgttgt gg                                             22

<210> SEQ ID NO 6
<211> LENGTH: 22
<212> TYPE: DNA
<213> ORGANISM: Artificial Sequence
<220> FEATURE:
```

```
<223> OTHER INFORMATION: bisulfite converted human sequence

<400> SEQUENCE: 6
tccggaaaga tgaccgttgc gg                                              22

<210> SEQ ID NO 7
<211> LENGTH: 24
<212> TYPE: DNA
<213> ORGANISM: Artificial Sequence
<220> FEATURE:
<223> OTHER INFORMATION: bisulfite converted human sequence

<400> SEQUENCE: 7
caaaaccaca caaaaatacc ctaa                                            24

<210> SEQ ID NO 8
<211> LENGTH: 24
<212> TYPE: DNA
<213> ORGANISM: Artificial Sequence
<220> FEATURE:
<223> OTHER INFORMATION: bisulfite converted human sequence

<400> SEQUENCE: 8
ccagggcacc cctgcgtggt tctg                                            24

<210> SEQ ID NO 9
<211> LENGTH: 22
<212> TYPE: DNA
<213> ORGANISM: Artificial Sequence
<220> FEATURE:
<223> OTHER INFORMATION: bisulfite converted human sequence

<400> SEQUENCE: 9
tggatgtggg gttgtatatt tg                                              22

<210> SEQ ID NO 10
<211> LENGTH: 22
<212> TYPE: DNA
<213> ORGANISM: Artificial Sequence
<220> FEATURE:
<223> OTHER INFORMATION: bisulfite converted human sequence

<400> SEQUENCE: 10
cggacgcggg gctgtacacc tg                                              22

<210> SEQ ID NO 11
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 11
caccaccaac acctccttct                                                 20

<210> SEQ ID NO 12
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 12
agaaggaggt gctggcggtg                                                 20
```

```
<210> SEQ ID NO 13
<211> LENGTH: 22
<212> TYPE: DNA
<213> ORGANISM: Artificial Sequence
<220> FEATURE:
<223> OTHER INFORMATION: bisulfite converted human sequence

<400> SEQUENCE: 13
ttggttgttt gtttggaggt ta                                              22

<210> SEQ ID NO 14
<211> LENGTH: 22
<212> TYPE: DNA
<213> ORGANISM: Artificial Sequence
<220> FEATURE:
<223> OTHER INFORMATION: bisulfite converted human sequence

<400> SEQUENCE: 14
ctggccgtcc gcctggaggt ca                                              22

<210> SEQ ID NO 15
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 15
ccaatcccaa tacaccacct                                                 20

<210> SEQ ID NO 16
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 16
aggtggtgca ctgggaccgg                                                 20

<210> SEQ ID NO 17
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 17
ttgtgggtgg ttaggaggat                                                 20

<210> SEQ ID NO 18
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 18
ctgcgggcgg ccaggaggac                                                 20

<210> SEQ ID NO 19
<211> LENGTH: 20
<212> TYPE: DNA
<213> ORGANISM: Artificial Sequence
<220> FEATURE:
<223> OTHER INFORMATION: bisulfite converted human sequence
```

```
<400> SEQUENCE: 19
cccacaaacc ccacactaac                                          20

<210> SEQ ID NO 20
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 20
gccagtgtgg ggtctgcggg                                          20

<210> SEQ ID NO 21
<211> LENGTH: 23
<212> TYPE: DNA
<213> ORGANISM: Artificial Sequence
<220> FEATURE:
<223> OTHER INFORMATION: bisulfite converted human sequence

<400> SEQUENCE: 21
ggaggaagtt gtgtgtgagt ttt                                      23

<210> SEQ ID NO 22
<211> LENGTH: 23
<212> TYPE: DNA
<213> ORGANISM: Artificial Sequence
<220> FEATURE:
<223> OTHER INFORMATION: bisulfite converted human sequence

<400> SEQUENCE: 22
ggaggaagcc gcgcgtgagc ctt                                      23

<210> SEQ ID NO 23
<211> LENGTH: 22
<212> TYPE: DNA
<213> ORGANISM: Artificial Sequence
<220> FEATURE:
<223> OTHER INFORMATION: bisulfite converted human sequence

<400> SEQUENCE: 23
cctcaacctt caacaacaac aa                                       22

<210> SEQ ID NO 24
<211> LENGTH: 22
<212> TYPE: DNA
<213> ORGANISM: Artificial Sequence
<220> FEATURE:
<223> OTHER INFORMATION: bisulfite converted human sequence

<400> SEQUENCE: 24
ttgccgtcgt cgaaggccga gg                                       22

<210> SEQ ID NO 25
<211> LENGTH: 17
<212> TYPE: DNA
<213> ORGANISM: Artificial Sequence
<220> FEATURE:
<223> OTHER INFORMATION: bisulfite converted human sequence

<400> SEQUENCE: 25
gtaaaacgac ggccagt                                             17

<210> SEQ ID NO 26
<211> LENGTH: 20
```

```
<212> TYPE: DNA
<213> ORGANISM: Artificial Sequence
<220> FEATURE:
<223> OTHER INFORMATION: bisulfite converted human sequence

<400> SEQUENCE: 26
gtgcaggcca cagtaatggt                                               20

<210> SEQ ID NO 27
<211> LENGTH: 18
<212> TYPE: DNA
<213> ORGANISM: Artificial Sequence
<220> FEATURE:
<223> OTHER INFORMATION: bisulfite converted human sequence

<400> SEQUENCE: 27
cttcgacgac ggcaactt                                                 18

<210> SEQ ID NO 28
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 28
tgtgtggttg tgtgggattt                                               20

<210> SEQ ID NO 29
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 29
cgcgcggtcg tgcgggaccc                                               20

<210> SEQ ID NO 30
<211> LENGTH: 24
<212> TYPE: DNA
<213> ORGANISM: Artificial Sequence
<220> FEATURE:
<223> OTHER INFORMATION: bisulfite converted human sequence

<400> SEQUENCE: 30
ccacctctac aaaaacctaa ccat                                          24

<210> SEQ ID NO 31
<211> LENGTH: 24
<212> TYPE: DNA
<213> ORGANISM: Artificial Sequence
<220> FEATURE:
<223> OTHER INFORMATION: bisulfite converted human sequence

<400> SEQUENCE: 31
acggccaggc tctcgtagag gtgg                                          24

<210> SEQ ID NO 32
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 32
```

```
tttgggtggt tgttggtttt                                              20

<210> SEQ ID NO 33
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 33
cccgggcggc tgccggtccc                                              20

<210> SEQ ID NO 34
<211> LENGTH: 23
<212> TYPE: DNA
<213> ORGANISM: Artificial Sequence
<220> FEATURE:
<223> OTHER INFORMATION: bisulfite converted human sequence

<400> SEQUENCE: 34
aaactcacac acaacttcct cct                                          23

<210> SEQ ID NO 35
<211> LENGTH: 23
<212> TYPE: DNA
<213> ORGANISM: Artificial Sequence
<220> FEATURE:
<223> OTHER INFORMATION: bisulfite converted human sequence

<400> SEQUENCE: 35
aggaggaagc cgcgcgtgag cct                                          23

<210> SEQ ID NO 36
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 36
agaccacaag gaggagaagc                                              20

<210> SEQ ID NO 37
<211> LENGTH: 23
<212> TYPE: DNA
<213> ORGANISM: Artificial Sequence
<220> FEATURE:
<223> OTHER INFORMATION: bisulfite converted human sequence

<400> SEQUENCE: 37
gctttcttca gaatggaaca ttt                                          23

<210> SEQ ID NO 38
<211> LENGTH: 21
<212> TYPE: DNA
<213> ORGANISM: Artificial Sequence
<220> FEATURE:
<223> OTHER INFORMATION: bisulfite converted human sequence

<400> SEQUENCE: 38
ttcctgagtc aacggaaact t                                            21

<210> SEQ ID NO 39
<211> LENGTH: 20
<212> TYPE: DNA
<213> ORGANISM: Artificial Sequence
```

```
<220> FEATURE:
<223> OTHER INFORMATION: bisulfite converted human sequence

<400> SEQUENCE: 39
ctgtagatga cacgccagca                                                    20

<210> SEQ ID NO 40
<211> LENGTH: 19
<212> TYPE: DNA
<213> ORGANISM: Artificial Sequence
<220> FEATURE:
<223> OTHER INFORMATION: bisulfite converted human sequence

<400> SEQUENCE: 40
tgctggcgtg tcatctaca                                                     19

<210> SEQ ID NO 41
<211> LENGTH: 19
<212> TYPE: DNA
<213> ORGANISM: Artificial Sequence
<220> FEATURE:
<223> OTHER INFORMATION: bisulfite converted human sequence

<400> SEQUENCE: 41
cgggggttaa aggctgata                                                     19

<210> SEQ ID NO 42
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 42
gttgctgaaa cagccaaggt                                                    20

<210> SEQ ID NO 43
<211> LENGTH: 21
<212> TYPE: DNA
<213> ORGANISM: Artificial Sequence
<220> FEATURE:
<223> OTHER INFORMATION: bisulfite converted human sequence

<400> SEQUENCE: 43
cacagtcaca gagtccacgt c                                                  21

<210> SEQ ID NO 44
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 44
caggccaagg agaaaaacaa                                                    20

<210> SEQ ID NO 45
<211> LENGTH: 20
<212> TYPE: DNA
<213> ORGANISM: Artificial Sequence
<220> FEATURE:
<223> OTHER INFORMATION: bisulfite converted human sequence

<400> SEQUENCE: 45
ctagagggca gcctcctctg                                                    20
```

<210> SEQ ID NO 46
<211> LENGTH: 27
<212> TYPE: DNA
<213> ORGANISM: Homo sapiens
<220> FEATURE:
<223> OTHER INFORMATION: bisulfite converted human sequence

<400> SEQUENCE: 46
acaaccaggg gctggccctg acaatgg                                              27

<210> SEQ ID NO 47
<211> LENGTH: 27
<212> TYPE: DNA
<213> ORGANISM: Homo sapiens
<220> FEATURE:
<223> OTHER INFORMATION: bisulfite converted human sequence

<400> SEQUENCE: 47
acaaccaggg gctggccctg acaatgg                                              27

<210> SEQ ID NO 48
<211> LENGTH: 27
<212> TYPE: RNA
<213> ORGANISM: Homo sapiens
<220> FEATURE:
<223> OTHER INFORMATION: bisulfite converted human sequence

<400> SEQUENCE: 48
acaaccaggg gcuggcccug acaaugg                                              27

<210> SEQ ID NO 49
<211> LENGTH: 27
<212> TYPE: RNA
<213> ORGANISM: Homo sapiens
<220> FEATURE:
<223> OTHER INFORMATION: bisulfite converted human sequence

<400> SEQUENCE: 49 ccaugucag ggccagcccc ugguugu                                               27

<210> SEQ ID NO 50
<211> LENGTH: 27
<212> TYPE: RNA
<213> ORGANISM: Artificial Sequence
<220> FEATURE:
<223> OTHER INFORMATION: bisulfite converted human sequence

<400> SEQUENCE: 50
auaauuaggg guugguuuug auaaugg                                              27

<210> SEQ ID NO 51
<211> LENGTH: 27
<212> TYPE: RNA
<213> ORGANISM: Artificial Sequence
<220> FEATURE:
<223> OTHER INFORMATION: bisulfite converted human sequence

<400> SEQUENCE: 51
uuauuguuag gguuaguuuu ugguugu                                              27

<210> SEQ ID NO 52
<211> LENGTH: 27
<212> TYPE: DNA
<213> ORGANISM: Artificial Sequence
<220> FEATURE:
<223> OTHER INFORMATION: bisulfite converted human sequence

<400> SEQUENCE: 52
ataattaggg gttggttttg ataatgg    27

<210> SEQ ID NO 53
<211> LENGTH: 27
<212> TYPE: DNA
<213> ORGANISM: Artificial Sequence
<220> FEATURE:
<223> OTHER INFORMATION: bisulfite converted human sequence

<400> SEQUENCE: 53
ttattgttag ggttagtttt tggttgt    27

<210> SEQ ID NO 54
<211> LENGTH: 27
<212> TYPE: DNA
<213> ORGANISM: Artificial Sequence
<220> FEATURE:
<223> OTHER INFORMATION: bisulfite converted human sequence

<400> SEQUENCE: 54
ataattaggg gttggttttg ataatgg    27

<210> SEQ ID NO 55
<211> LENGTH: 27
<212> TYPE: DNA
<213> ORGANISM: Artificial Sequence
<220> FEATURE:
<223> OTHER INFORMATION: bisulfite converted human sequence

<400> SEQUENCE: 55
ttattgttag ggttagtttt tggttgt    27

<210> SEQ ID NO 56
<211> LENGTH: 27
<212> TYPE: DNA
<213> ORGANISM: Artificial Sequence
<220> FEATURE:
<223> OTHER INFORMATION: bisulfite converted human sequence

<400> SEQUENCE: 56
tattaatccc caaccaaaac tattacc    27

<210> SEQ ID NO 57
<211> LENGTH: 27
<212> TYPE: DNA
<213> ORGANISM: Artificial Sequence
<220> FEATURE:
<223> OTHER INFORMATION: bisulfite converted human sequence

<400> SEQUENCE: 57
aataacaatc ccaatcaaaa accaaca    27